United States Patent
Ranchod et al.

(10) Patent No.: US 8,876,754 B2
(45) Date of Patent: Nov. 4, 2014

(54) CATHETER WITH FILTERING AND SENSING ELEMENTS

(75) Inventors: Arun Ranchod, Ellwood City, PA (US); David M. Griffiths, Pittsburgh, PA (US); Alan D. Hirschman, Glenshaw, PA (US)

(73) Assignee: Bayer Medical Care Inc., Indianola, PA (US)

( * ) Notice: Subject to any disclaimer, the term of this patent is extended or adjusted under 35 U.S.C. 154(b) by 2129 days.

(21) Appl. No.: 11/469,054

(22) Filed: Aug. 31, 2006

(65) Prior Publication Data

US 2008/0097339 A1 Apr. 24, 2008

(51) Int. Cl.
*A61M 31/00* (2006.01)
*A61M 25/00* (2006.01)

(52) U.S. Cl.
CPC .................................. *A61M 25/007* (2013.01)
USPC .......................................... 604/65; 604/104

(58) Field of Classification Search
USPC ............. 604/65, 104; 606/200; 600/345, 348, 600/381
See application file for complete search history.

(56) References Cited

U.S. PATENT DOCUMENTS

| | | |
|---|---|---|
| 2,139,653 A | 12/1938 | Belfrage |
| 3,386,438 A | 6/1968 | Stevens |
| 3,674,033 A | 7/1972 | Powers |
| 3,695,457 A | 10/1972 | Cohen |
| 3,828,767 A | 8/1974 | Spiroff |
| 3,888,249 A | 6/1975 | Spencer |
| D236,920 S | 9/1975 | Sheridan |
| 4,002,174 A | 1/1977 | Reed et al. |
| 4,173,981 A | 11/1979 | Mortensen |
| 4,292,976 A | 10/1981 | Banka |
| 4,437,856 A | 3/1984 | Valli |
| 4,488,877 A | 12/1984 | Klein et al. |
| 4,552,127 A | 11/1985 | Schiff |
| 4,557,724 A | 12/1985 | Gregonis et al. |
| 4,639,246 A | 1/1987 | Dudley |

(Continued)

FOREIGN PATENT DOCUMENTS

| | | |
|---|---|---|
| EP | 0346012 | 12/1989 |
| EP | 0609950 | 8/1994 |

(Continued)

OTHER PUBLICATIONS

EV3, Technology and Variation Brochure, 2006 ev3, Inc.

(Continued)

*Primary Examiner* — Kevin C Sirmons
*Assistant Examiner* — Phillip Gray
(74) *Attorney, Agent, or Firm* — Joseph L. Kent

(57) ABSTRACT

A delivery apparatus useful for infusing a therapeutic agent into a body lumen, the apparatus including a lumenal body defining at least one infusion port for infusing the therapeutic agent into the body lumen, and a sensing element which is distal of the at least one infusion port and adapted to sense the amount of infused therapeutic agent or any compound derived therefrom in the body lumen. Another embodiment of the apparatus includes a lumenal body defining at least one infusion port for infusing the therapeutic agent into the body lumen, and a filtration element which is distal of the at least one infusion port and adapted to deliver a reaction agent which may react with the therapeutic agent in the body lumen. A sensing element may be provided distal of the filtration element for sensing the amount of infused therapeutic agent or compounds derived therefrom in the body lumen.

34 Claims, 10 Drawing Sheets

(56) References Cited

U.S. PATENT DOCUMENTS

| | | |
|---|---|---|
| 4,645,488 A | 2/1987 | Matukas |
| 4,661,094 A | 4/1987 | Simpson |
| 4,680,029 A | 7/1987 | Ranford et al. |
| 4,687,471 A | 8/1987 | Twardowski et al. |
| 4,692,141 A | 9/1987 | Mahurkar |
| 4,701,166 A | 10/1987 | Groshong et al. |
| 4,718,425 A | 1/1988 | Tanaka et al. |
| 4,769,016 A | 9/1988 | Labianca |
| 4,770,652 A | 9/1988 | Mahurkar |
| 4,772,269 A | 9/1988 | Twardowski et al. |
| 4,784,638 A | 11/1988 | Ghajar et al. |
| 4,787,882 A | 11/1988 | Claren |
| 4,801,297 A | 1/1989 | Mueller |
| 4,808,155 A | 2/1989 | Mahurkar |
| 4,824,436 A | 4/1989 | Wolinsky |
| 4,863,441 A | 9/1989 | Lindsay et al. |
| 4,917,667 A | 4/1990 | Jackson |
| 4,935,004 A | 6/1990 | Cruz |
| 4,961,731 A | 10/1990 | Bodicky et al. |
| 4,988,058 A | 1/1991 | Dirscherl et al. |
| 5,048,033 A | 9/1991 | Donahue et al. |
| 5,057,073 A | 10/1991 | Martin |
| 5,078,702 A | 1/1992 | Pomeranz |
| 5,085,635 A | 2/1992 | Cragg |
| 5,087,244 A | 2/1992 | Wolinsky et al. |
| 5,098,413 A | 3/1992 | Trudell et al. |
| 5,147,334 A | 9/1992 | Moss |
| 5,180,387 A | 1/1993 | Ghajar et al. |
| 5,197,951 A | 3/1993 | Mahurkar |
| 5,207,655 A | 5/1993 | Sheridan |
| 5,221,255 A | 6/1993 | Mahurkar et al. |
| 5,224,938 A | 7/1993 | Fenton, Jr. |
| 5,250,034 A | 10/1993 | Appling et al. |
| 5,267,979 A | 12/1993 | Appling et al. |
| 5,300,022 A | 4/1994 | Klapper et al. |
| 5,330,433 A | 7/1994 | Fonger et al. |
| 5,336,178 A | 8/1994 | Kaplan et al. |
| 5,348,536 A | 9/1994 | Young et al. |
| 5,364,373 A | 11/1994 | Waskonig et al. |
| 5,370,653 A | 12/1994 | Cragg |
| 5,370,685 A | 12/1994 | Stevens |
| 5,374,245 A | 12/1994 | Mahurkar |
| 5,380,307 A | 1/1995 | Chee et al. |
| 5,403,291 A | 4/1995 | Abrahamson |
| 5,451,206 A | 9/1995 | Young |
| 5,484,423 A | 1/1996 | Waskonig et al. |
| 5,485,831 A | 1/1996 | Holdsworth et al. |
| 5,489,278 A | 2/1996 | Abrahamson |
| 5,509,428 A | 4/1996 | Dunlop |
| 5,531,679 A | 7/1996 | Schulman et al. |
| 5,531,700 A | 7/1996 | Moore et al. |
| 5,536,261 A | 7/1996 | Stevens |
| 5,556,390 A | 9/1996 | Hicks |
| 5,558,644 A | 9/1996 | Boyd et al. |
| 5,578,006 A | 11/1996 | Schon |
| 5,584,803 A | 12/1996 | Stevens et al. |
| 5,591,137 A | 1/1997 | Stevens |
| 5,599,328 A | 2/1997 | Stevens |
| 5,616,137 A | 4/1997 | Lindsay |
| 5,643,226 A | 7/1997 | Cosgrove et al. |
| 5,643,228 A | 7/1997 | Schucart et al. |
| 5,651,170 A | 7/1997 | Stevens |
| 5,662,619 A | 9/1997 | Zarate |
| 5,695,457 A | 12/1997 | St. Goar et al. |
| 5,702,368 A | 12/1997 | Stevens et al. |
| 5,738,652 A | 4/1998 | Boyd et al. |
| 5,766,151 A | 6/1998 | Valley et al. |
| 5,769,812 A | 6/1998 | Stevens et al. |
| 5,792,094 A | 8/1998 | Stevens et al. |
| 5,800,407 A | 9/1998 | Eldor |
| 5,800,408 A | 9/1998 | Strauss et al. |
| 5,807,318 A | 9/1998 | St. Goar et al. |
| 5,807,349 A | 9/1998 | Person et al. |
| 5,814,016 A | 9/1998 | Valley et al. |
| 5,830,196 A | 11/1998 | Hicks |
| 5,843,050 A | 12/1998 | Jones et al. |
| 5,868,702 A | 2/1999 | Stevens et al. |
| 5,873,865 A | 2/1999 | Horzewski et al. |
| 5,876,383 A | 3/1999 | Grooters et al. |
| 5,885,238 A | 3/1999 | Stevens et al. |
| 5,904,670 A | 5/1999 | Schreiner |
| 5,904,932 A | 5/1999 | De Vringer |
| 5,913,842 A | 6/1999 | Boyd et al. |
| 5,914,193 A | 6/1999 | Ono et al. |
| 5,916,193 A | 6/1999 | Stevens et al. |
| 5,921,957 A | 7/1999 | Killion et al. |
| 5,930,169 A | 7/1999 | Iwata et al. |
| 5,947,985 A | 9/1999 | Imran |
| 5,957,901 A | 9/1999 | Mottola et al. |
| 5,976,114 A | 11/1999 | Jonkman et al. |
| 6,022,363 A | 2/2000 | Walker et al. |
| 6,029,671 A | 2/2000 | Stevens et al. |
| 6,053,932 A | 4/2000 | Daniel et al. |
| 6,132,405 A | 10/2000 | Nilsson et al. |
| 6,152,141 A | 11/2000 | Stevens et al. |
| 6,179,816 B1 | 1/2001 | Mottla et al. |
| 6,186,987 B1 | 2/2001 | Grooters |
| 6,197,014 B1 | 3/2001 | Samson et al. |
| 6,254,578 B1 | 7/2001 | Grooters et al. |
| 6,280,413 B1 | 8/2001 | Clark et al. |
| 6,280,423 B1 | 8/2001 | Davey et al. |
| 6,290,692 B1 | 9/2001 | Klima et al. |
| 6,293,958 B1 | 9/2001 | Berry et al. |
| 6,319,242 B1 | 11/2001 | Patterson et al. |
| 6,332,892 B1 | 12/2001 | Desmond, III et al. |
| 6,350,253 B1 | 2/2002 | Deniega et al. |
| 6,432,091 B1 | 8/2002 | Davey |
| 6,442,413 B1 * | 8/2002 | Silver ............................ 600/345 |
| 6,524,300 B2 | 2/2003 | Meglin |
| 6,527,979 B2 | 3/2003 | Constantz et al. |
| 6,592,519 B1 * | 7/2003 | Martinez ....................... 600/309 |
| 6,605,061 B2 | 8/2003 | VanTassel et al. |
| 6,635,027 B1 | 10/2003 | Cragg et al. |
| 6,652,548 B2 * | 11/2003 | Evans et al. ................... 606/159 |
| 6,663,613 B1 | 12/2003 | Evans et al. |
| 6,663,650 B2 | 12/2003 | Sepetka et al. |
| 6,669,679 B1 | 12/2003 | Savage et al. |
| 6,682,508 B1 | 1/2004 | Meythaler et al. |
| 6,730,104 B1 | 5/2004 | Sepetka et al. |
| 6,749,619 B2 | 6/2004 | Ouriel et al. |
| 6,755,813 B2 | 6/2004 | Ouriel et al. |
| 6,805,692 B2 | 10/2004 | Muni et al. |
| 6,936,025 B1 | 8/2005 | Evans et al. |
| 6,949,087 B2 | 9/2005 | VanTassel et al. |
| 6,969,373 B2 | 11/2005 | Schwartz et al. |
| 7,670,327 B2 | 3/2010 | Kucharczyk et al. |
| 7,697,972 B2 * | 4/2010 | Verard et al. .................. 600/424 |
| 2001/0001117 A1 | 5/2001 | Chow |
| 2003/0045865 A1 * | 3/2003 | Knapp ........................ 604/890.1 |
| 2003/0158516 A1 | 8/2003 | Wholey et al. |
| 2003/0199819 A1 | 10/2003 | Beck |
| 2004/0024358 A1 | 2/2004 | Meythaler et al. |
| 2004/0133184 A1 * | 7/2004 | Hildebrand ..................... 604/65 |
| 2004/0167385 A1 | 8/2004 | Rioux et al. |
| 2006/0224179 A1 | 10/2006 | Kucharczyk et al. |

FOREIGN PATENT DOCUMENTS

| | | |
|---|---|---|
| FR | 2550454 | 2/1985 |
| JP | 11276593 | 10/1999 |
| WO | 9505862 | 3/1995 |
| WO | 9713543 | 4/1997 |
| WO | 2005/049110 | 6/2005 |

OTHER PUBLICATIONS

U.S. Appl. No. 60/520,071, filed Nov. 15, 2003.
Office Action issued in corresponding application, Apr. 20, 2010.
International Preliminary Report on Patentability and Written Opinion issued in corresponding PCT Publication No. WO 2005/049110, Aug. 25, 2006.
Tillman, "510(k) Summary, Acist Plus 4 Angiographic Catheter", Apr. 26, 2002.

(56) References Cited

OTHER PUBLICATIONS

Daniel et al., "A Solution to the Problem of High-Flow Jest from Minature Angiographic Catheters", American Roentgen Ray Society, May 1990, pp. 1091-1095, vol. 154.

Hansen et al., "New High-Flow "Cloud" Catheter for Safer Delivery of Contrast Material", Radiology, 1989, pp. 461-464, vol. 179.
European Search Report issued in corresponding application, Feb. 7, 2008.

* cited by examiner

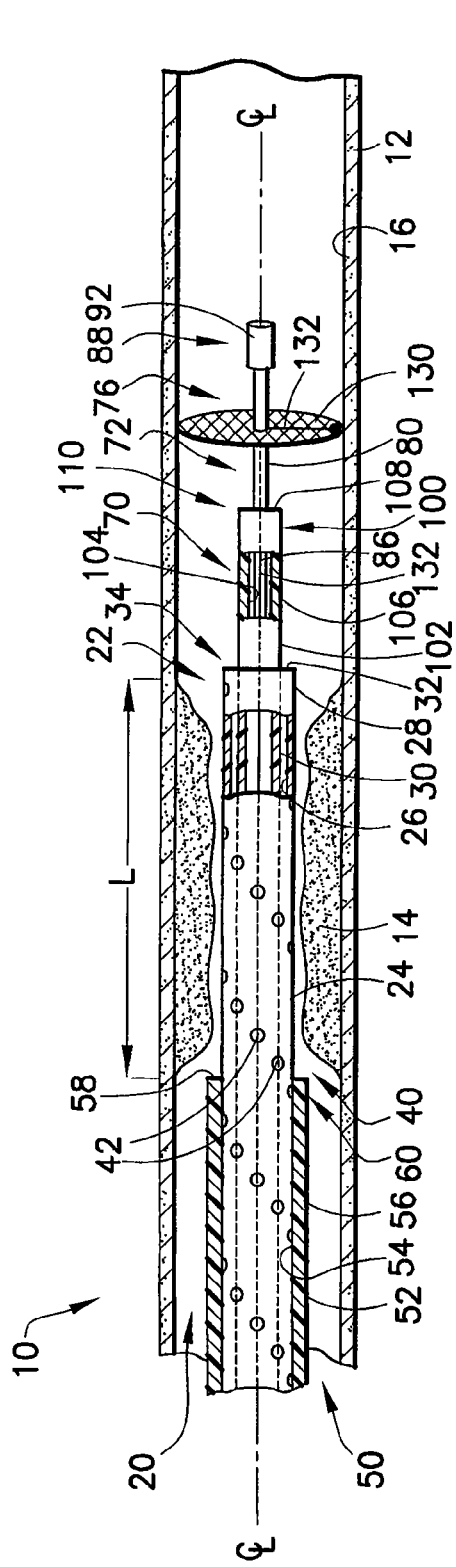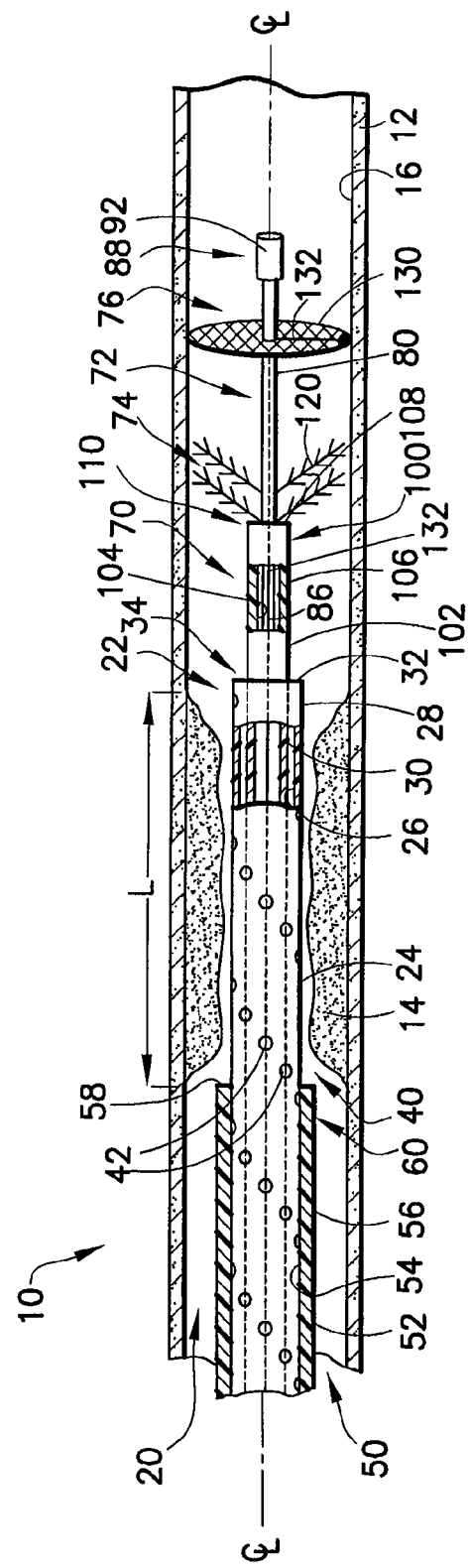
FIG.2
FIG.3

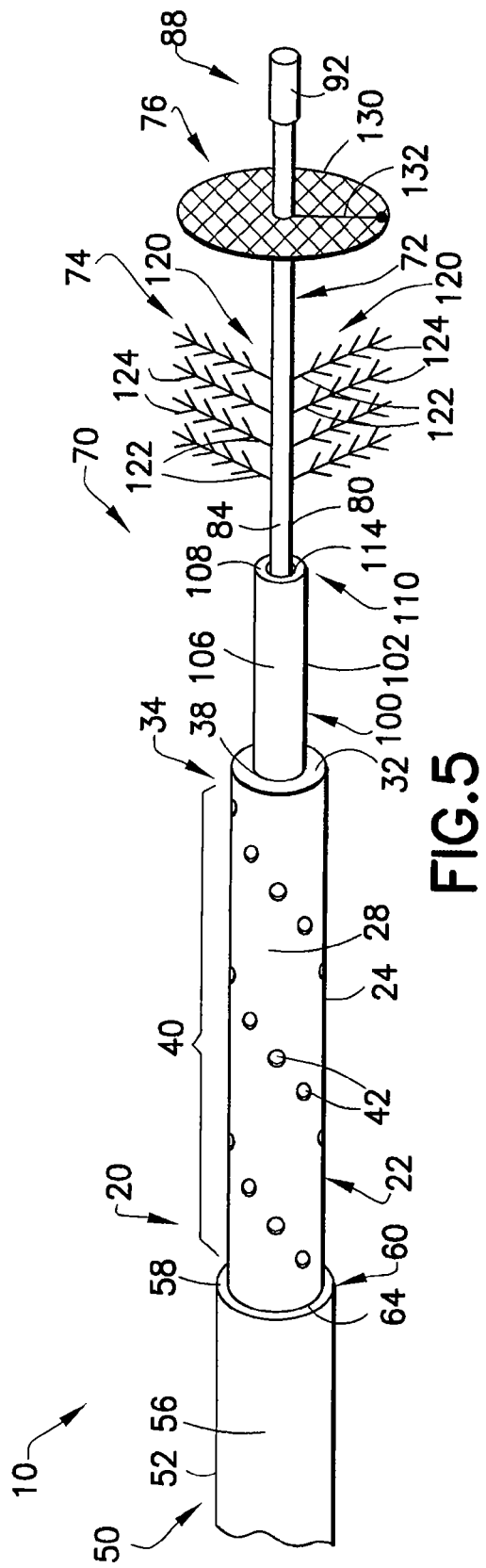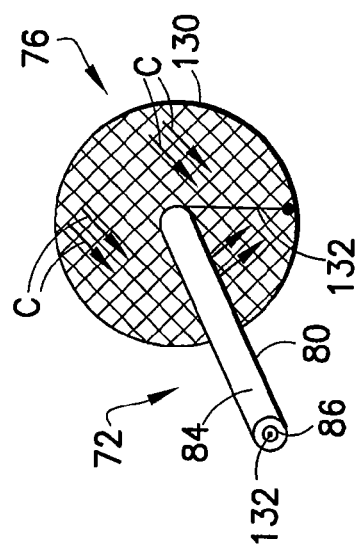

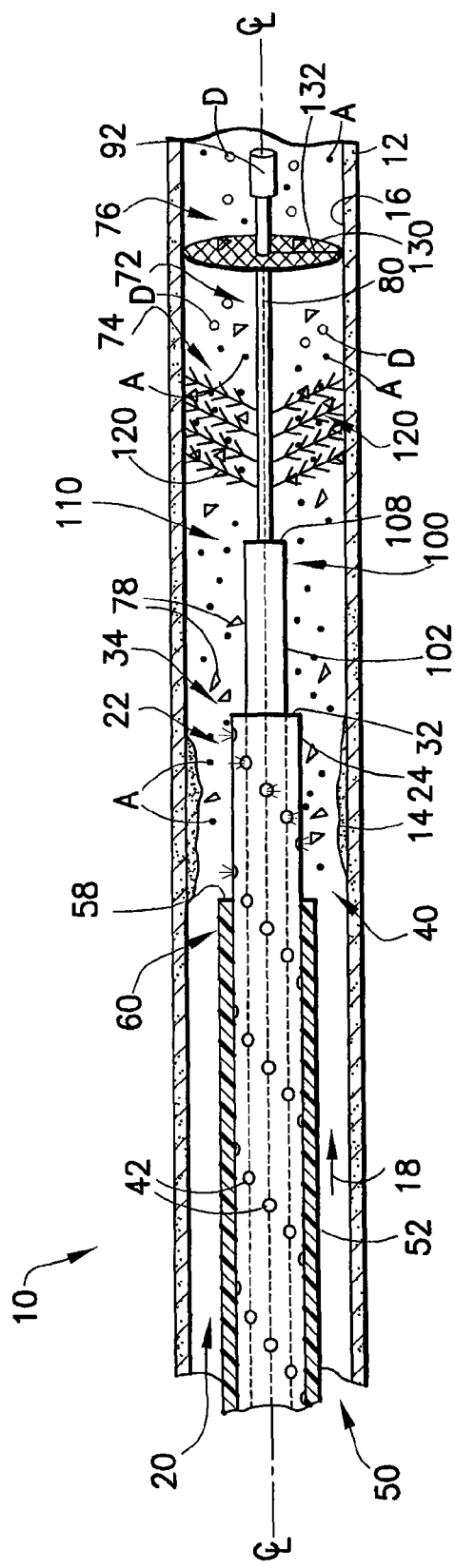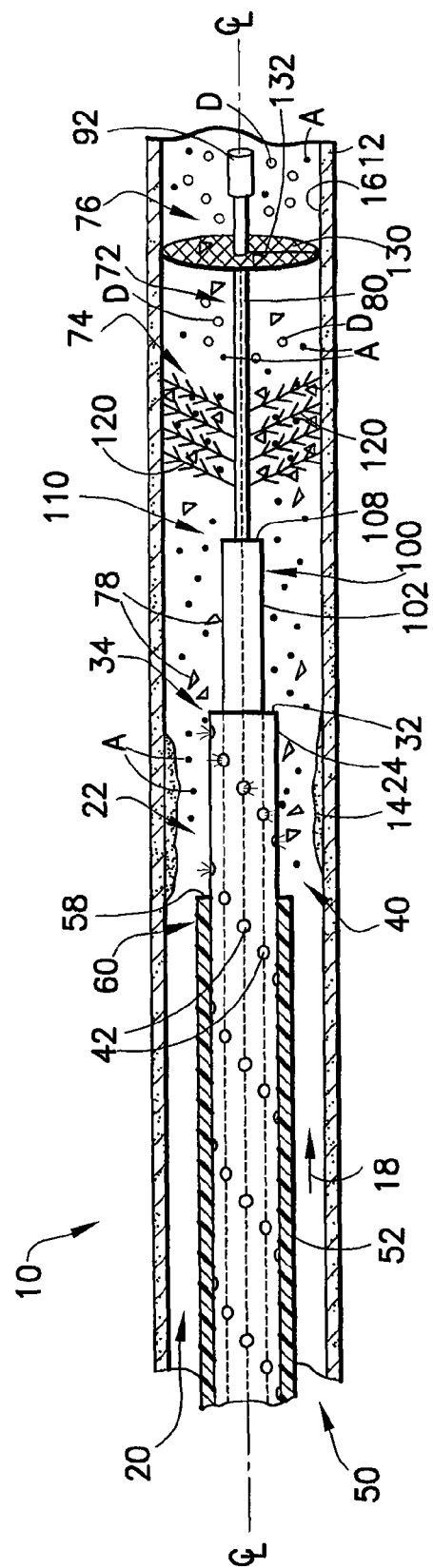

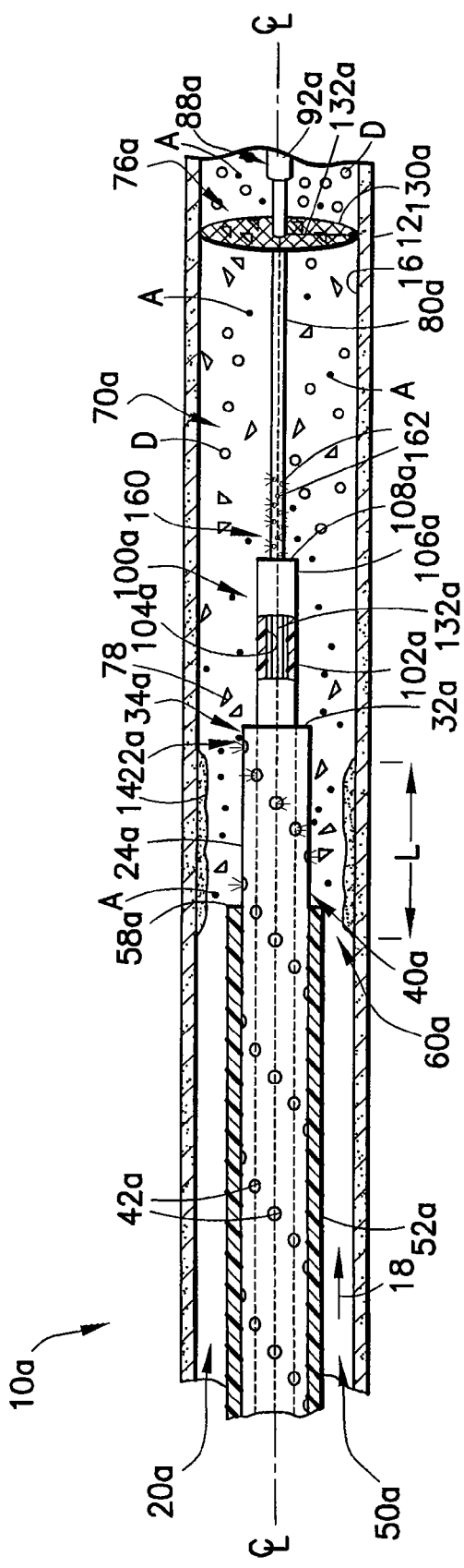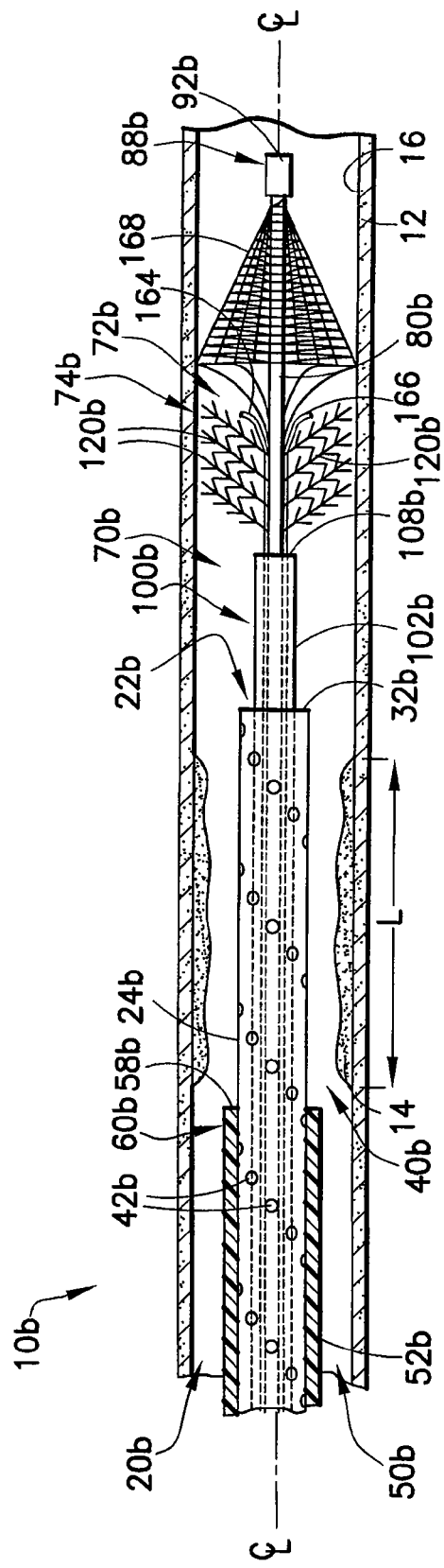

CATHETER WITH FILTERING AND SENSING ELEMENTS

BACKGROUND OF THE INVENTION

1. Field of the Invention

The field of endeavor relates generally to medical devices and methods. More particularly, the filed of endeavor relates to medical devices and methods for infusing therapeutic agents into a body lumen, such as a blood vessel, for treating disorders or conditions present in the body lumen, such as dissolving and disrupting occlusive materials from the blood vessel wall.

2. Description of Related Art

Thrombosis and atherosclerosis are common ailments which occur in humans and which result from the deposition of thrombus within the lumen of blood vessels. When hardened, such deposits are commonly referred to as plaque or clots. Such deposits are common in the peripheral blood vessels that feed the limbs of the human body and the coronary arteries which feed the heart. Stasis, incompetent valves, and trauma in the venous circulation can cause thrombosis, particularly occurring as a deep vein thrombosis in the peripheral vasculature. When such deposits accumulate in localized regions of the blood vessel, they can restrict blood flow and cause a serious health risk. Thrombosis can develop in cerebral vessels, as well, and be the source of ischemic strokes.

In addition to forming in the natural vasculature, thrombosis is a serious problem in "artificial" blood vessels, particularly in peripheral femoral-popliteal and coronary bypass grafts and dialysis access grafts and fistulas. The creation of such artificial blood vessels requires anastomotic attachment at at least one, and usually at least two, locations in the vasculature. Such sites of an anastomotic attachment are particularly susceptible to thrombus formation due to narrowing caused by intimal hyperplasia, and thrombus formation at these sites is a frequent cause of failure of the implanted graft or fistula. The arterio-venous grafts and fistulas which are used for dialysis access are significantly compromised by thrombosis at the sites of anastomotic attachment and elsewhere. Thrombosis often occurs to such an extent that the graft needs to be replaced within a few years or, in the worst cases, a few months.

A variety of methods have been developed for treating thrombosis and atherosclerosis in the coronary and peripheral vasculature as well as in implanted grafts and fistulas. Such techniques include surgical procedures, such as coronary artery bypass grafting, and minimally invasive procedures, such as angioplasty, atherectomy, thrombectomy, thrombolysis, transmyocardial revasculaturization, and the like.

A variety of techniques have been developed for dissolving clots using thrombolytic agents, such as tissue plasminogen activator (tPA), streptokinase, urokinase, and the like. Thrombolytic agents can be very effective at attacking and dissolving relatively soft clots, such as that formed in deep veins. Such agents, however, require time to act, and local delivery catheters often employ isolation balloons to provide high local concentrations of the active thrombolytic agents. Even with such enhanced concentrations, the agents can take extended periods to act, rendering the treatments lengthy and inefficient. In some instances, extensive regions of clot simply cannot be effectively treated using thrombolytic agents alone. In such cases, it has been further proposed to provide a mechanical element to disrupt the clot while the thrombolytic agents are being delivered. An example of such a mechanical approach is disclosed, for example, in U.S. Pat. No. 5,947,985 to Mir A. Imran which describes a catheter having axially spaced-apart balloons for isolating a treatment region within a blood vessel. The catheter also includes a port for delivering thrombolytic agent between the spaced-apart balloons and a helical wire for removing clot material from the blood vessel wall to assist in aspiration.

As will be appreciated from the foregoing, it is known that because of blood flow through blood vessels, drugs and therapeutic agents delivered to the site of an angioplasty procedure, for example, can be rapidly dissipated and removed from the delivery site before they can be absorbed in sufficient quantities to become effective. Catheters have therefore been developed to directly deliver drugs to the desired site and maintain the drugs there. In some cases, the treatment catheter includes delivery ports or other structures that bear against the occluded site within the blood vessel and conduct a thrombolytic agent directly to the occluded site as disclosed in U.S. Pat. No. 5,904,670 to Schreiner. U.S. Pat. No. 6,280,413 to Clark et al. discloses a thrombolytic agent and drug delivery catheter with an expanding portion which is adapted to bear against and deliver the thrombolytic agent directly to the occluded site.

U.S. Pat. No. 5,087,244 to Wolinsky et al. discloses a catheter with a flexible balloon having a plurality of minute openings. The balloon can be inflated by heparin. As the wall of the balloon contacts the arterial wall, the heparin exits the balloon, directly on the walls. However, the balloon can block the perfusion of blood distal to the delivery site, depriving downstream tissue of needed blood. This limits the amount of time available for drug delivery. The inflation of the balloon can also damage the arterial wall, promoting restenosis. In addition, since the balloon is inflated by the heparin, heparin can leak out before the arterial wall is contacted, wasting the drug. The balloon further needs to be deflated prior to removal or to allow blood flow. The pressure required to deflate the balloon could also draw blood into the balloon, preventing further use of the catheter until the blood has been removed. U.S. Pat. No. 4,824,436, also to Wolinsky, discloses a drug delivery catheter comprising a pair of occlusion balloons for securing the catheter in position and isolating a region of the artery which has been opened by percutaneous translumenal coronary angioplasty (PTCA), and a drug delivery conduit for delivering heparin under pressure into the region isolated by the occlusion balloons. The pressure of the heparin forces the heparin to coat and penetrate the arterial tissue. This configuration presents similar perfusion problems to those discussed previously in connection with U.S. Pat. No. 5,087,244 to Wolinsky et al. The heparin, therefore, is only delivered for about 5-60 seconds which may be inadequate for sufficient absorption. U.S. Pat. No. 5,336,178 to Kaplan et al. discloses a catheter with drug delivery ribs which are brought into contact with the walls of the blood vessel lumen by an inflatable balloon. A series of ports in the catheter shaft are provided proximal to the balloon to allow for perfusion of blood through the catheter shaft.

Due to the possibility of damaging the blood vessel wall, other devices (i.e., catheters) combine the ability to deliver or infuse a thrombolytic agent with simple agitation within the blood vessel to remove the thrombus and thus avoid inflatable balloon type delivery systems. U.S. Pat. No. 6,663,613 to Evans et al. discloses a catheter which combines the ability to deliver or infuse a thrombolytic agent into a blood vessel with an agitation action which mechanically disrupts the clot forming the occlusion in the blood vessel. Another patent, U.S. Pat. No. 6,936,025 to Evans et al., combines the delivery of a lysing agent to a blood vessel with a low frequency vibration motion of the catheter body to achieve clot dislocation/disruption.

It is well-known that if a portion of the thrombus separates from the blood vessel wall and is transported through the cardiovascular system, it can cause an embolism, or blockage of a blood vessel. A thrombus in a deep vein in the leg can cause a pulmonary embolism. A thrombus in a coronary artery can cause myocardial infarction. Similarly, a thrombus in a cerebral artery can cause cerebral infarction (i.e., ischemic stroke). As a result, devices have been developed which attempt to filter dislodged thrombus or thrombotic material during therapeutic procedures such as the delivery of thrombolytic agents to a blood vessel to minimize the chance of a dislodged thrombus causing significant damage to the patient. A typical form of these devices is as a filter "net" which intercepts the dislodged thrombus or thrombotic material is disclosed in U.S. Pat. No. 6,053,932 to Daniel et al. which discloses an emboli capturing system adapted to catch emboli in blood vessels. This patent discloses a microporous mesh formed of woven or braided fibers or wires, or a microporous membrane, for capturing the dislodged emboli/thrombus. Another such filter "net" is disclosed in U.S. Patent Application Publication No. 2003/0199819 to Beck, which discloses a balloon catheter with downstream "safety net" that prevents any dislodged material from migrating through a patient's bloodstream. Often, "net" type devices are used in combination with a catheter having a suction capability such that dislodged thrombus is sucked into a lumen in the catheter with the mesh or net structure provided mainly for redundant safety purposes. Such a catheter having suction capability is disclosed in U.S. Pat. No. 6,805,692 to Muni et al. One known catheter apparatus includes multiple infusion ports for delivering a thrombolytic agent to a blood vessel with several of the infusion ports provided within a filter basket for delivering the thrombolytic agent in the area defined by the filter basket to dissolve any dislodged thrombus trapped in the filter, (See U.S. Pat. Nos. 6,755,813 and 6,749,619 to Ouriel et al.).

Catheters are also known in the medical field for sensing and providing feedback data relating to physiological data concerning the patient. For example, U.S. Pat. No. 4,552,127 to Schiff discloses a balloon catheter with a stylet having a distal end coupled to an EKG electrode. The stylet extends through the catheter body to couple the EKG electrode to a proximal end of the catheter body and, thus, to the exterior of the patient's body. U.S. Pat. No. 6,319,242 to Patterson et al. discloses a catheter device with a proximity sensor to alert the user/operator of the location of the distal end of the catheter and its proximity to a stent implanted in a blood vessel wall. U.S. Pat. No. 6,682,508 to Meythaler et al. discloses a central nervous system catheter assembly comprising multiple lumens including a drug delivery branch and a monitoring/sensing branch. The monitoring/sensing branch is adapted for sensing and providing feedback information related to intracranial pressure. U.S. Patent Application Publication No. 2004/0167385 to Rioux et al. discloses a catheter with a sensor adapted to measure one or more physiological parameters associated with the status of a blood vessel, including: pressure, flow rate, temperature, fluid velocity, physical dimensions, vessel compliance, pH saline content, gas content, etc.

SUMMARY OF THE INVENTION

Based on the foregoing, it would be desirable to provide improved apparatus and methods for infusing therapeutic agents into a body lumen, such as a blood vessel, for treating disorders or conditions present in the body lumen, such as dissolving and disrupting occlusive materials from the blood vessel wall and further be able to neutralize the harmful effects of the infused agent. It would further be desirable to provide apparatus and methods which can enhance the delivery of thrombolytic agents to a region of a blood vessel wall where thrombus or an occlusion in the form of a clot is present without inhibiting natural blood flow to a significant degree.

In one form, the therapeutic agent delivery apparatus is used for infusing a therapeutic agent into a body lumen and comprises a lumenal body defining at least one and optionally a plurality of infusion ports for infusing the therapeutic agent into the body lumen, and a sensing element distal of the at least one/plurality of infusion ports and adapted to sense the amount, for example concentration, of infused therapeutic agent or any compound derived from the therapeutic agent in the body lumen.

A feedback component may be associated with the sensing element and adapted to provide a sensing element signal to a location outside of the body lumen. The feedback component may provide the sensing element signal to a user interface, for example, connected to a proximal end of the lumenal body. The sensing element signal may be represented to a user as an audible, visual, or tactile stimulus or a combination stimulus comprising one or more of the audible, visual, and tactile stimuli. The sensing element signal may be proportional to the amount, for example concentration, of therapeutic agent or derivative thereof sensed by the sensing element.

The sensing element may be adapted to sense the amount, for example concentration, of therapeutic agent or derivative thereof by one or more of resonant mass detection, light reflectance, and electrical conductivity changes. Sensing element may further be adapted to sense the amount, for example concentration, of therapeutic agent via thermal detection principles such as injecting the therapeutic agent at a temperature higher or lower than human body temperature and measuring thermal changes in the physiological fluid in the body lumen. Ion selective electrodes may also be used as part of sensing element or as sensing element itself. The sensing element may be shaped to correspond to the cross-sectional shape of the body lumen, for example, a generally circular shape that stretches across or fills the body lumen.

The sensing element may be formed as a fine wire mesh, for example, and adapted to intercept at least some of the therapeutic agent or derivative thereof in the body lumen. Additionally, the sensing element may be formed of electrically conductive material, for example, in the form of a fine wire mesh. The electrically conductive material may change conductivity when exposed to the therapeutic agent or derivative thereof.

A filtration element may be disposed distal of the at least one infusion port and proximal of the sensing element. Such a filtration element may comprise tree-like/shaped filtration structures. A second, inner lumenal body may be coaxial with the lumenal body and comprise a portion proximal of the sensing element defining at least one distal infusion port for infusing the therapeutic agent, a different therapeutic agent, or a reaction agent adapted to react with the therapeutic agent into the body lumen.

In another form, the apparatus includes a lumenal body defining at least one and optionally a plurality of infusion ports for infusing the therapeutic agent into the body lumen, and a filtration element distal of the infusion ports and adapted to deliver a reaction agent adapted to react with the therapeutic agent in the body lumen.

In one embodiment, the filtration element may be coated with the reaction agent. In another embodiment, the filtration element may comprise a plurality of generally tree-shaped structures which are, for example, coated with the reaction agent. In a further embodiment, the filtration element may be in the form of at least one distal infusion port disposed distal or downstream of the lumenal body for infusing the reaction agent into the body lumen. Moreover, a sensing element may be provided distal or downstream of the at least one distal infusion port.

A sensing element may be provided distal of the filtration element. The sensing element is adapted to sense the amount, for example concentration, of infused therapeutic agent or any compound derived from the therapeutic agent in response to the reaction agent in the body lumen. A feedback component may be associated with the sensing element. The feedback component may be adapted to provide a sensing element signal to a location outside of the body lumen. The feedback component may provide the sensing element signal to a user interface, for example, connected to a proximal end of the lumenal body. The sensing element signal may be represented to a user as an audible, visual, or tactile stimulus or a combination stimulus comprising one or more of an audible, visual, and tactile stimuli. The sensing element signal may be proportional to the amount, for example concentration, of therapeutic agent or derivative thereof sensed by the sensing element.

The sensing element may be adapted to sense the amount, for example concentration, of therapeutic agent or derivative thereof by one or more of resonant mass detection, light reflectance, and electrical conductivity changes. The sensing element may be shaped to correspond to the cross-sectional shape of the body lumen, for example, a generally circular shape that stretches across or fills the body lumen.

The sensing element may be formed as a fine wire mesh, for example, and adapted to intercept at least some of the therapeutic agent or derivative thereof in the body lumen. Additionally, the sensing element may be formed of electrically conductive material, for example, in the form of a fine wire mesh. The electrically conductive material may change conductivity when exposed to the therapeutic agent or derivative thereof.

A further aspect relates to a sensing element for use with a lumenal body used to deliver a therapeutic agent to a body lumen. The sensing element generally comprises an electrically conductive body structure adapted to change conductivity when exposed to the therapeutic agent or any compound derived from the therapeutic agent. The body of the sensing element may be in the form of an electrically conductive fine wire mesh. The body of the sensing element may also be shaped to correspond to the cross-sectional shape of the body lumen, for example, a generally circular shape that stretches across or fills the body lumen. The sensing element may comprise a feedback component adapted to provide a sensing element signal to a location outside of the body lumen. The sensing element may optionally include a user interface coupled to the feedback component for receiving the sensing element signal. Such a user interface may be adapted to represent the sensing element signal to a user as an audible, visual, or tactile stimulus or a combination stimulus comprising one or more of the audible, visual, and tactile stimuli. The sensing element signal may be proportional to the amount, for example concentration, of therapeutic agent or derivative thereof sensed by the sensing element. The sensing element may be adapted to sense a combination of a therapeutic agent and a reaction agent adapted to react with the therapeutic agent Another aspect relates to a filtration element for use with a lumenal body used to deliver a therapeutic agent to a body lumen. The filtration element may comprise a plurality of structures coated with a reaction agent adapted to react with the therapeutic agent. Such filtration structures may be coated structures that are generally tree-shaped in configuration.

A method of infusing a therapeutic agent into a body lumen using the therapeutic agent delivery apparatus is also an concept described herein. In one embodiment, the method comprises inserting a lumenal body into the body lumen, the lumenal body defining at least one infusion port for infusing the therapeutic agent into the body lumen; infusing the therapeutic agent into the body lumen; and sensing the amount, for example concentration, of infused therapeutic agent or any compound derived from the therapeutic agent in the body lumen with a sensing element disposed distal of the at least one infusion port.

The method may comprise providing a sensing element signal to a location outside the body lumen with a feedback component associated with the sensing element. Such a sensing element signal may be provided to a user interface, for example, connected to a proximal end of the lumenal body. The sensing element signal may be represented to a user as an audible, visual, or tactile stimulus or a combination stimulus comprising one or more of the audible, visual, and tactile stimuli. The sensing element signal may be proportional to the amount, for example concentration, of therapeutic agent or derivative thereof sensed by the sensing element. In one form, the sensing element is adapted to sense the amount, for example concentration, of therapeutic agent or derivative thereof by one or more of resonant mass detection, light detection, and electrical conductivity changes.

An aspect of the method may comprise intercepting at least some of the therapeutic agent or derivative thereof in the body lumen with the sensing element. Another aspect of the method may comprise infusing additional therapeutic agent, a different therapeutic agent, or a reaction agent adapted to react with the therapeutic agents into the body lumen through at least one distal infusion port proximal of the sensing element. A further aspect may comprise filtering the therapeutic agent or derivative thereof in the body lumen with a filtration element disposed distal of the infusion ports and proximal of the sensing element.

Another embodiment of the method of infusing a therapeutic agent into a body lumen generally comprises inserting a lumenal body into the body lumen, the lumenal body defining at least one infusion port for infusing the therapeutic agent into the body lumen; infusing the therapeutic agent into the body lumen; and delivering a reaction agent adapted to react with the therapeutic agent in the body lumen with a filtration element disposed distal of the at least one infusion port. The reaction agent may be coated on the filtration element and filtering of the therapeutic agent occurs by contact between the coated filtration element and the therapeutic agent.

The reaction agent may be delivered by infusing the reaction agent through at least one distal infusion port forming the filtration element. The method may comprise sensing the amount, for example concentration, of infused therapeutic agent or any compound derived from the therapeutic agent in response to the reaction agent in the body lumen with a sensing element disposed distal of the at least on distal infusion port.

Additionally, the method may comprise sensing the amount, for example concentration, of infused therapeutic agent or any compound derived from the therapeutic agent in response to the reaction agent in the body lumen with a sensing element disposed distal of the filtration element. A sensing element signal may be provided to a location outside the body lumen with a feedback component associated with the sensing element. As an example, the sensing element signal may be provided to a user interface, for example, connected to a proximal end of the lumenal body. The sensing element signal may be represented to a user as an audible, visual, or tactile stimulus or a combination stimulus comprising one or more of the audible, visual, and tactile stimuli. The sensing element signal may be proportional to the amount, for example concentration, of therapeutic agent or derivative thereof sensed by the sensing element. The sensing element may sense the amount, for example concentration, of therapeutic agent or derivative thereof by one or more of resonant mass detection, light reflectance, and electrical conductivity changes. An aspect of the method may comprise intercepting at least some of the therapeutic agent or derivative thereof in the body lumen with the sensing element.

Further details and advantages will become clear upon reading the following detailed description in conjunction with the accompanying drawing figures, wherein like parts are identified with like reference numerals throughout.

BRIEF DESCRIPTION OF THE DRAWINGS

FIG. 2 is a longitudinal cross-sectional view of a distal end portion of the catheter of FIG. 1 shown indwelling in a blood vessel requiring treatment.

FIG. 3 is a longitudinal cross-sectional view of the distal end portion of the catheter of FIG. 2 and showing a filtration element in a partially deployed state and a sensing element in a fully deployed state.

FIG. 5 is a perspective view of the distal end portion of the catheter of FIG. 1 showing the filtration element and sensing element each in a fully deployed state.

FIG. 6 is a perspective view of a portion of the distal end portion of the catheter of FIG. 5 showing operational aspects of the sensing element.

FIG. 10A is a longitudinal cross-sectional view of the distal end portion of the catheter of FIG. 2 showing operation of the catheter in another mode and the results of the delivered therapeutic agent on the thrombus.

FIG. 11A is a longitudinal cross-sectional view of the distal end portion of the catheter of FIG. 2 showing operation of the catheter in a third mode and the results of the delivered therapeutic agent on the thrombus.

FIG. 13 is a longitudinal cross-sectional view of the alternative catheter embodiment of FIG. 12 showing operation of the catheter and the results of the delivered therapeutic agent on the thrombus.

FIG. 14 is a longitudinal cross-sectional view of the catheter of FIG. 1 according to a third embodiment.

DESCRIPTION OF THE PREFERRED EMBODIMENTS

Figure 1:
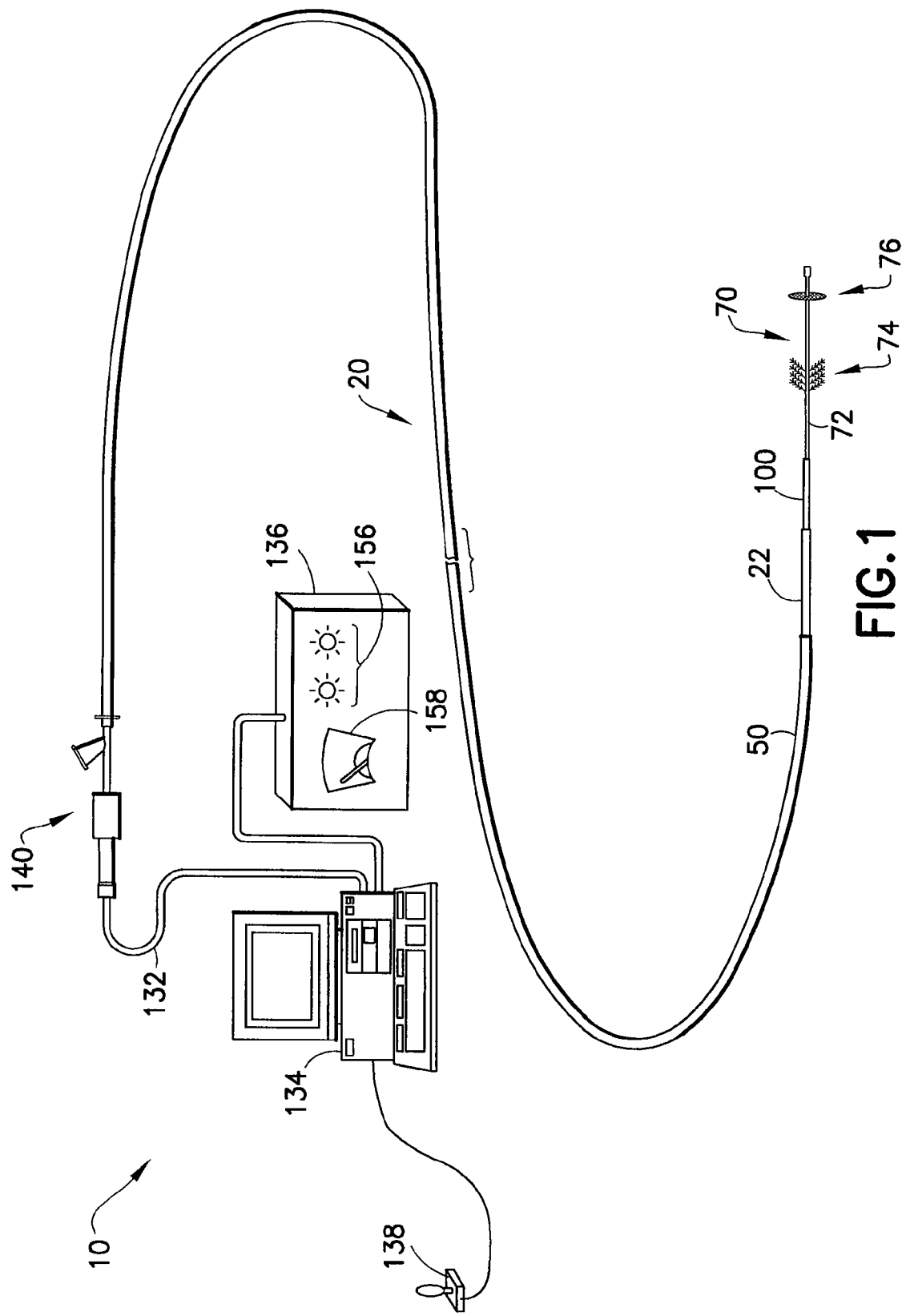
FIG. 1 is a perspective view of an embodiment of an intralumenal catheter system including a control device and an optional auxiliary display device.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific devices illustrated in the accompanying drawing figures and described herein are simply exemplary and should not be considered as limiting.

A general aspect described herein relates to an apparatus and method for providing a therapeutic substance such as a therapeutic agent or drug or, typically in liquid form, to a body lumen for treating a disorder or condition present in the body lumen and thereafter removing or intercepting the substance and/or neutralizing or rendering inert any harmful aspects of the therapeutic substance to prevent damage to healthy tissue in the body lumen and/or limit or eliminate or minimize any possible harmful effects to downstream tissues and organs. The body lumen may be a blood vessel such as an artery in which atherosclerosis is present, which is the result of the deposition of occluding deposits within the lumen of the blood vessel. When hardened, such deposits or "thrombus" are commonly referred to as plaque, clots, or occlusions. Other lumens or cavities or body regions which may be treated by the apparatus and method described herein include the urethra, bladder, prostate, rectum, bile duct, pancreatic duct and central nervous system, such as along the spinal column, as examples. Drugs or other therapeutic agents may be provided conceivably to any body lumen or cavity to treat a variety of disorders or conditions in the body lumen using the physical structures and methods described herein. Accordingly, the foregoing listing of lumens/cavities is not intended to be exhaustive. Hereinafter, "therapeutic agent" is intended to be a term encompassing any substance intended to treat a disorder or condition present in a body lumen or cavity. Two specific therapeutic agents, thrombolytic agent for treating thrombus present in a blood vessel and doxorubicin for treating cancerous tumors, will be discussed in this disclosure as a vehicle to describe structural and operational aspects of the apparatus and methods. However, these two specific therapeutic agents are not intended to be limiting and are cited for exemplary purposes only.

In one embodiment, the apparatus is an intralumenal catheter adapted to provide a therapeutic agent to a body lumen such as a blood vessel to treat a disorder or condition present in the body lumen such as a thrombus which causes atherosclerosis in the blood vessel. As an example, the catheter provides the therapeutic agent to treat the thrombus at or near the location of the thrombus in the blood vessel. A feature of the catheter relates to using the natural flow of physiological fluid in the body lumen, in the present case blood flowing in a blood vessel, so that the therapeutic agent is transported by action of the natural flow of fluid. Accordingly, the therapeutic agent may be carried by the natural flow of fluid from the catheter to the treatment site and possibly beyond the treatment site. The carrying of therapeutic agent by a naturally occurring physiological fluid stream may be termed natural or passive fluid transport.

Another feature of the catheter relates to a filtration apparatus or element being located at a distal or downstream location from the location of therapeutic agent infusion which is used to intercept and inhibit the harmful effects of the therapeutic agent with mechanical and/or chemical filtration features or elements. For example, it is known that some therapeutic agents, such as tissue plasminogen activator (tPA) used as a thrombolytic agent and doxorubicin for treating cancerous tumors, can have adverse effects on healthy body tissue and/or generally cause negative downstream effects. Accordingly, it is desirable to localize the application of such therapeutic agents to the affected area within the body lumen. The distal filtration element may use a combination of mechanical filtration structure(s) and chemical filtration to filter and/or render inert or harmless via chemical reaction the infused therapeutic agent to substantially "remove" the infused agent or in effect substantially remove the harmful consequences of the therapeutic agent on the body lumen. As indicated previously, the natural flow of physiological fluid in the body lumen may be used to passively transport the therapeutic agent to the filtration element where the therapeutic agent naturally "washes" over the filtration element which mechanically and/or chemically substantially removes or renders substantially harmless or inert the deleterious effects of the therapeutic agent. Typically, such passive chemical filtration occurs by a chemical reaction between the therapeutic agent and another substance adapted to react with the therapeutic agent (i.e., a reaction agent) to render substantially harmless the deleterious effects of the therapeutic agent. Such a substance may be referred to as a "neutralizing" or "inhibiting" or "reaction" agent and these terms may be used interchangeably herein. However, "reaction agent" is generally used herein as a term used to described any substance which reacts with the therapeutic agent in manner that renders the therapeutic agent harmless or transformed for other purposes, such as to facilitate sensing of chemical compounds in the body lumen. Moreover, the neutralizing or inhibiting or reaction agent may be adapted to bind to the therapeutic agent thereby trapping the therapeutic agent in the mechanical filtration structures. It will be appreciated that the neutralizing or inhibiting or reaction agent may be delivered in liquid form to chemically react with the therapeutic agent but could also be part of the mechanical filtration structures such a solid or liquid coating on the structure or structures. The mechanical filtration structures may further be a biomaterial with an interfacial layer or portion adapted to chemically react with the therapeutic agent, for example, to cause the therapeutic agent to bind to the mechanical filtration structures. In such a situation, mechanical and chemical filtration may be accomplished by the same structure or structures.

Another feature of the catheter relates to a sensing apparatus or element being located distal or downstream of the filtration element which is used to sense the amount, typically concentration, of therapeutic agent remaining in the body lumen and/or a compound derived from the chemical reaction between the therapeutic agent and the neutralizing or inhibiting agent or reaction agent discussed previously. The sensing element senses the therapeutic agent and/or derived compound and provides a signal indicative of the amount of therapeutic agent remaining or neutralized in the body lumen downstream of the filtration element. This signal may then be used to quantify the amount of therapeutic agent remaining in the body lumen such as a blood vessel and, further, be displayed to the operator of the catheter. The signal may be displayed or communicated to the catheter operator to provide real-time or near real-time quantitative information regarding the amount of therapeutic agent injected, remaining in the body lumen, and/or neutralized. If desired, a specific agent or substance may be provided as part of the chemical filtration feature of the filtration element to chemically react with the therapeutic agent and, for example, bind with the therapeutic agent. This combined or derived chemical substance may be adapted to interact with the sensing element to cause a specific response, for example a signal, to be communicated by the sensing element to the operator. As an example, the derived or combined substance may have a component that is specifically adapted to interact with the sensing element to elicit a signal from the sensing element which represents the amount of therapeutic agent injected, remaining in the body lumen, and/or neutralized. Communication to the operator may be by visual, audible, tactile, or a combination of visual, audible, and tactile conveyances. For example, the sensing element signal may be communicated via wires or wirelessly to a control device or a display device or other user interface which visually alerts or displays information regarding the amount of therapeutic agent injected, remaining in the body lumen, and/or neutralized. The display may, for example, be part of a computer or other control device. Such a device may include a mechanism to audibly convey the information to the operator and/or a tactile device, such as a hand-held device, to convey the information to the operator tactilely. Specific examples of conveyances for providing feedback to the catheter operator are detailed herein. Moreover, the signal may also be used as a basis or input to the control device which can warn of an unsafe condition like an excessive amount of therapeutic agent concentration in the body lumen, and the control device may use this information to control, for example reduce the amount of therapeutic agent delivered, or cease delivery altogether of the therapeutic agent.

With the foregoing introduction in mind, one embodiment is an apparatus and method for performing thrombolysis in a body lumen and, more particularly, as an apparatus and method for delivering an infusate in the form of a thrombolytic agent into a blood vessel to dissolve thrombus causing atherosclerosis in the blood vessel. Referring initially to FIGS. 1-6, such as an infusate-delivering device is an intralumenal catheter apparatus 10 for delivering an infusate, thrombolytic agent in this example, into a blood vessel 12 to dissolve thrombus 14 present in the blood vessel 12. As an example, thrombus 14 may be present in a cerebral blood vessel 12 and such a thrombus 14 has the potential of causing an ischemic stroke. Typically, ischemic strokes occur in the middle cerebral artery and, in the present embodiment, catheter 10 is sized to pass into the middle cerebral artery to deliver a therapeutic agent for dissolving thrombus 14. Accordingly, catheter 10 is a 3 or 4 French (Fr) catheter when used for this specific application. However, catheter 10 may be of a larger size to fit into larger blood vessels such as a 5 Fr catheter and larger.

As indicated previously, the exemplary structure and operation of catheter 10 will be described with catheter 10 delivering a thrombolytic agent "A", such as plasmin, tissue plasminogen activator (tPA), streptokinase, urokinase, and the like to blood vessel 12 to treat thrombus 14. Other known thrombolytic agents A include alteplase, reteplase, tenecteplase, staphylokinase, and desmoteplase. However, these specific thrombolytic agents should not be considered as an exhaustive listing, and catheter 10 is suited to delivering a number of therapeutic agents to blood vessel 12 to treat thrombus 14 or for treating other abnormalities and conditions in blood vessel 12 or for other purposes. It is generally known that thrombolytic agents such as plasmin, tPA, and the like can damage healthy arterial tissue, downstream organs and tissue, and, in the present circumstance, an oversupplying of thrombolytic agent A in cerebral blood vessel 12 may act upon "downstream" thrombus (not shown) resulting in dislodging of the thrombus or pieces thereof which could be responsible for inducing ischemic strokes. A feature of the catheter 10 relates to a filtration apparatus or element being located at a distal or downstream location from where the thrombolytic agent A is delivered to blood vessel 12. This filtration element as described herein is used to intercept the thrombolytic agent A with mechanical and/or chemical filtration and neutralize or inhibit the harmful effects of the thrombolytic agent A. This filtration element or structure, described in detail herein, is provided as part of catheter 10 and is used to mechanically filter and/or chemically neutralize or render inert injected or infused thrombolytic agent A to prevent damage to the non-thrombolized portion of blood vessel 12, downstream tissue and organs, and prevent the dissolution and dislodgement of downstream thrombus which could cause ischemic stroke (in the present circumstance), pulmonary embolism, or coronary embolism.

Thrombus 14 is adhered to an inner surface 16 of blood vessel 12 and undesirably restricts blood flow through the blood vessel 12, also known as arteriolosclerosis. Additionally, thrombus 14 or portions thereof place the patient at risk of ischemic stroke if the thrombus 14 or portions thereof break-off from inner surface 16 and travel through and become lodged in downstream cerebral blood vessels. Thrombus 14 extends along the inner surface 16 of the blood vessel 12 over an axial length L. Catheter 10 is generally adapted to treat thrombus 14 by injecting thrombolytic agent A in the axial region or area defined by length L to dissolve the thrombus 14. The direction of natural blood flow in blood vessel is designated by arrow 18 in the various drawing figures.

Figure 7:
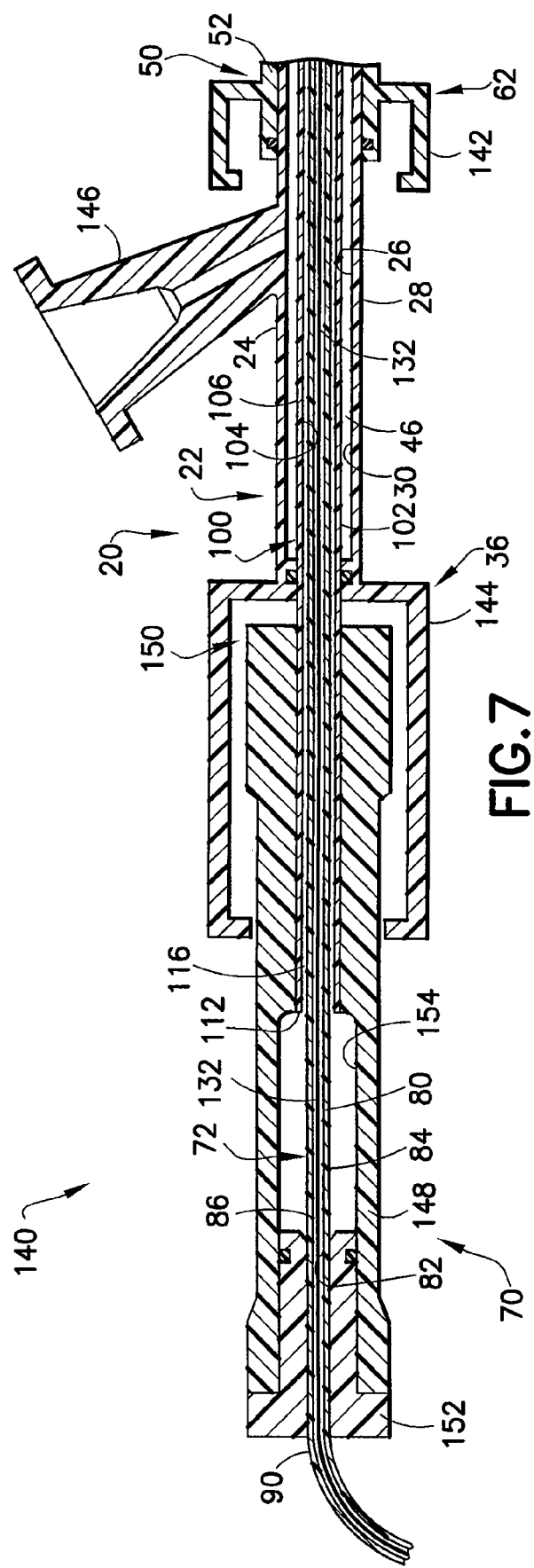
FIG. 7 is a longitudinal cross-sectional view of a proximal end portion of the catheter of FIG. 1.

Catheter 10 comprises multiple coaxial catheter assemblies or devices generally divisible into first and second (i.e., outer and inner) catheters assemblies 20 and 70 that extend coaxially along a central longitudinal axis $C_L$ of catheter 10. First or outer catheter 20 forms the outer catheter portion of catheter 10 and is disposed about second or inner catheter 70. First catheter 20 comprises an inner fluid delivery catheter 22 surrounded by an outer sheath or first sheath catheter 50. Fluid delivery catheter 22 is a tubular member formed by a lumenal body 24 having inner and outer surfaces 26 and 28. Inner surface 26 defines a first lumen 30 that extends through lumenal body 24 of fluid delivery catheter 22. An end wall 32 is provided at a distal end 34 of lumenal body 24 of fluid delivery catheter 22 and extends between inner and outer surfaces 26 and 28. A proximal end 36 of lumenal body 24 of fluid delivery catheter 22 is shown in FIG. 7 discussed herein. End wall 32 defines a distal opening 38 through which second catheter 70 projects or extends. End wall 32 seals around second catheter 70 to prevent or minimize fluid leakage through distal opening 38.

Fluid delivery catheter 22 has an infusion section 40 that includes a plurality of infusion ports 42 defined in lumenal body 24 for delivering thrombolytic agent A to the vicinity of thrombus 14. Infusion section 40 may have any suitable length as measured from distal end 34 of lumenal body 24 of fluid delivery catheter 22 to treat thrombus 14. Infusion ports 42 extend through first lumen 30 from inner surface 26 to outer surface 28 of lumenal body 24 and are spaced axially apart. In the illustrated embodiment, infusion ports 42 extend axially along infusion section 40 in a helical pattern but could alternatively extend in another suitable pattern. Another suitable distribution pattern for infusion ports 42 in infusion section 40 is disclosed in U.S. Provisional Patent Application No. 60/520,071, filed Nov. 15, 2003, and PCT Patent Application No. PCT/US2004/038093 (WO 2005/049110) each entitled "Catheter for Diagnostic Imaging and Therapeutic Purposes" and assigned to the same assignee as the present application and are incorporated herein by reference in their entirety. These Applications further disclose suitable size and infusion port "density" distribution information for infusion ports 42. If desired, infusion ports 42 may vary in size, for example, increase in diameter toward distal end 34 of lumenal body 24 of fluid delivery catheter 22. Having infusion ports 42 increase in size from proximal end 36 (FIG. 7) toward distal end 34 may provide a more evenly distributed flow pattern throughout infusion section 40 because the fluid pressure inside first lumen 30 drops both from frictional losses and from the thrombolytic agent A escaping through the more proximally-located infusion ports 42 along the axial length of lumenal body 24 of fluid delivery catheter 22. As an example, infusion ports 42 may be adapted to deliver infuisate, in this case thrombolytic agent A, at a flow rate of up to 200 cc/hr. However, in the case of tPA as the thrombolytic agent A, delivery rates and treatment amounts are governed by Food and Drug Administration (FDA) regulations.

A first annular space 46 is defined between the inner diameter of lumenal body 24 of fluid delivery catheter 22 and the outer diameter of second catheter 70 described herein. Annular space 46 permits the flow of thrombolytic agent A through first lumen 30 defined by lumenal body 24 of fluid delivery catheter 22 to reach infusion section 40 and infusion ports 42 in particular, and subsequent injection or delivery of the thrombolytic agent A into blood vessel 12 and the region of blood vessel 12 in which thrombus 14 is present. As described further herein in connection with FIG. 7, the thrombolytic agent A is introduced into first lumen 30 at proximal end 36 of lumenal body 24 of fluid delivery catheter 22 and flows through annular space 46 defined in the first lumen 30 under pressure until reaching infusion section 40 and infusion ports 42.

Outer sheath 50 coaxially surrounds fluid delivery catheter 22. Fluid delivery catheter 22 and outer sheath 50 are axially movable relative to one another. Fluid delivery catheter 22 is axially movable relative to outer sheath 50 so that distal end 34 and fluid infusion section 40 of lumenal body 24 of the fluid delivery catheter 22 are projectable or extendable outward from outer sheath 50. However, outer sheath 50 may be retractable relative to fluid delivery catheter 22 to achieve the same exposed configuration of fluid infusion section 40 of lumenal body 24 of fluid delivery catheter 22. Outer sheath 50 is also a tubular member comprising a lumenal body 52 having inner and outer surfaces 54 and 56. An end wall 58 is provided at a distal end 60 of lumenal body 52 of outer sheath 50 and extends between inner and outer surfaces 54 and 56. A proximal end 62 of lumenal body of outer sheath 50 is shown in FIG. 7 discussed herein. End wall 58 defines a distal opening 64 through which fluid delivery catheter 22 and second catheter assembly 70 project or extend. End wall 58 seals around lumenal body 24 of fluid delivery catheter 22 to prevent or minimize fluid leakage through distal opening 64. Inner surface 54 defines an inner diameter for lumenal body 52 of outer sheath 50 that is approximately equal to the outer diameter of lumenal body 24 of fluid delivery catheter 22. The close fit between outer sheath 50 and fluid delivery catheter 22 permits relative movement but substantially prevents fluid from exiting through any of the plurality of infusion ports 42 that are covered over by outer sheath 50. As described further herein, axial distal movement of fluid delivery catheter 22 relative to outer sheath 50, or optionally axial proximal movement of the outer sheath 50 relative to the fluid delivery catheter 22, enables the operator of catheter 10 to selectively uncover (or cover) a portion of the plurality of infusion ports 42 in lumenal body 24 in order to control the amount and distribution of thrombolytic agent A delivered by infusion section 40 of lumenal body 24 of fluid delivery catheter 22. Such axial movement of fluid delivery catheter 22 or outer sheath 50 varies the axial length of infusion section 40 exposed for the delivery of thrombolytic agent A. As may be seen by comparing FIGS. 2-4 with FIGS. 8-11, the exposed axial length of infusion section 40 may be varied to generally match the axial length L of thrombus 14.

Second catheter 70 is coaxially disposed within first catheter 20 and comprises a filtering and sensing catheter 72 surrounded by an inner sheath or second sheath catheter 100. Filtering and sensing catheter 72 comprises a filtration element or device 74 and a distally located sensing element or device 76. Filtration element 74 is generally adapted to expand radially outward upon deployment from inner sheath 100 and is further generally adapted to filter and trap dislodged thrombolytic material 78 which results when thrombolytic agent A is introduced into blood vessel 12 via fluid delivery catheter 22. Additionally, filtration element 74 is adapted to mechanically and/or chemically "filter" the thrombolytic agent A as described in further detail herein. Filtering and sensing catheter 72 is likewise a tubular member formed by a lumenal body 80 having inner and outer surfaces 82, 84. Inner surface 82 defines a second lumen 86 that extends through lumenal body 80 of filtering and sensing catheter 72. Lumenal body 80 has a distal end 88 and a proximal end 90 shown in FIG. 7 discussed herein. Lumenal body 80 terminates at distal end 88 with a flexible tip 92 which aids in guiding filtering and sensing catheter 72 within blood vessel 12 upon deployment from inner sheath 100 and first or outer catheter 20. Flexible tip 92 also encloses second lumen 86 at distal end 88 of lumenal body 80 of filtering and sensing catheter 72 to form an enclosed cavity within the lumenal body 80.

Inner sheath 100 coaxially surrounds filtering and sensing catheter 72. Filtering and sensing catheter 72 and inner sheath 100 are axially movable relative to one another. Filtering and sensing catheter 72 is axially movable relative to inner sheath 100 so that at least the portion of lumenal body 80 of the filtering and sensing catheter 72 supporting filtration element 74 and sensing element 76 may be extended distally from inner sheath 100 for deployment in blood vessel 12. Alternatively, inner sheath 100 may be configured to be retractable axially relative to filtering and sensing catheter 72 to achieve the same deployment arrangement for filtration element 74 and sensing element 76. Inner sheath 100 is also a tubular member comprising a lumenal body 102 having inner and outer surfaces 104 and 106. An end wall 108 is provided at a distal end 110 of lumenal body 102 of outer sheath 100 and extends between inner and outer surfaces 104 and 106. A proximal end 112 of inner sheath 100 is shown in FIG. 7 discussed herein. End wall 108 defines a distal opening 114 through which filtering and sensing catheter 72 projects or extends. End wall 108 seals around lumenal body 80 of filtering and sensing catheter 72 to prevent or minimize fluid entry into inner sheath 100 through distal opening 114. Inner surface 104 defines an inner diameter for lumenal body 102 of inner sheath 100 which permits passage of the filtering and sensing catheter 72 and defines a second annular space 116 between the inner diameter of the lumenal body 102 of the inner sheath 100 and the outer diameter of lumenal body 80 of the filtering and sensing catheter 72. As an alternative, the cooperative engagement between inner sheath 100 and filtering and sensing catheter 72 may be similar to the cooperative engagement between the outer sheath 50 and fluid delivery catheter 22. In this alternative configuration, the inner diameter of lumenal body 102 of inner sheath 100 may be approximately equal to the outer diameter of lumenal body 80 of filtering and sensing catheter 72. Such a close fit between inner sheath 100 and filtering and sensing catheter 72 is intended to still permit free relative movement between the inner sheath 100 and filtering and sensing catheter 72. End wall 108 seals around lumenal body 80 of filtering and sensing catheter 72 to prevent or minimize fluid entry through distal opening 114 into annular space 116 defined between inner sheath 100 and filtering and sensing catheter 72.

As described previously, second catheter 70 projects or extends through distal opening 36 in end wall 32 lumenal body 24 of fluid delivery catheter 22. In particular, end wall 32 seals around lumenal body 102 of inner sheath 100 to prevent or minimize fluid leakage through distal opening 36. Nonetheless, relative axial movement is permitted by the cooperative engagement of lumenal body 102 in distal opening 36. As shown in FIGS. 2-4 and 7, first annular space 46, as described previously, permits the flow of thrombolytic agent A through lumen 30 defined by lumenal body 24 of fluid delivery catheter 22. This flow passes through annular space 46 to reach infusion section 40 and infusion ports 42 in particular and is subsequently injected or delivered to blood vessel 12 and the region of blood vessel 12 in which the thrombus 14 is present. Second annular space 116 is optionally defined between the inner diameter of lumenal body 102 of inner sheath 100 and the outer diameter of lumenal body 80 of the filtering and sensing catheter 72.

Filtration element 74 is a radially expandable structure that is disposed about lumenal body 80 of filtering and sensing catheter 72. In one embodiment, filtration element 74 is comprised of a plurality of tree-like filtration structures 120 (hereinafter filtration structures 120) or a similar structure or structures that provide for mechanical filtration of fluid flow 18 in blood vessel 12 and copious surface area for a chemical coating, solid or liquid, with a chemical adapted to react with the thrombolytic agent A. In one instance, the chemical coating may be adapted to neutralize, inhibit, or render harmless the thrombolytic agent A, termed herein a "reaction agent", and bind the thrombolytic agent A to filtration structures 120, as schematically shown in FIG. 9B discussed herein. In another instance, the chemical coating may be adapted to neutralize, inhibit, or render harmless the thrombolytic agent A and bind the thrombolytic agent A to filtration structures 120 but also include another agent which combines with the thrombolytic agent A and which results in a combined or derived "D" compound that is specifically designed or adapted to be sensed by downstream sensing element 76, as shown schematically in FIG. 10B discussed herein. In a further instance, the chemical coating may possibly be adapted to convert the thrombolytic agent A to a non-harmful state or form and allow this converted or derived compound D to flow passively downstream or distal from filtration element 74 without binding to filtration structures 120, as shown schematically in FIG. 11B discussed herein. Each of the foregoing alternatives may be described or identified as "passive" chemical filtration discussed previously. Additionally, in each case the natural flow of physiological fluid, in this case blood flow, carries the thrombolytic agent A to filtration element 74 where mechanical and chemical filtration occurs. Mechanical filtration is primarily designed for the dissolved or dislodged thrombotic material 78 while passive chemical filtration is primarily designed for the neutralization or inhibiting of thrombolytic agent A. As an alternative to tree-like mechanical structures, filtration structures 120 could be an open-cell layer or structure, such as a sponge-like structure, that maximizes potential surface area for coating and filtration. The tree-shaped orientation or configuration of filtration structures 120 is intended to also represent such an open-cell layer or sponge-like structure in the Figures.

Filtration structures 120 each comprise a stem portion 122 and a plurality of branch members 124 which together define the tree-like appearance of filtration structures 120 which is suitable for mechanical filtering of dissolved thrombotic material 78. Stem portions 122 may be secured to the outer surface 84 of lumenal body 80 of filtering and sensing catheter 72 or be formed as part of the lumenal body 80. Filtration structures 120 are desirably made of a flexible solid elastic or superelastic material. One such material that is suitable for filtration structures 120 is Nitinol wire, or another memory metal material which can be preformed into a memorized shape and subsequently deformed into another shape. In the present embodiment, the outward or radially-extended configuration of filtration structures 120 is the memorized shape for filtration structures 120. The superelastic properties of the material of filtration structures 120 permit the filtration structures 120 to be deflected to a collapsed condition extending generally parallel to the central longitudinal axis $C_L$ of catheter 10 when it is desired to retract filtering and sensing catheter 72 into inner sheath 100 (or axially extend inner sheath 100 over filtering and sensing catheter 72) with minimal force and without damage to the filtration structures 120. It should be noted that filtration structures 120 could also be made from a shape memory material which can resume a memorized shape upon heating of the material. The heating of such a shape memory material may be done using electric current or other means applied to lumenal body 80 of filtering and sensing catheter 72, or through normal body heat.

Figure 4:
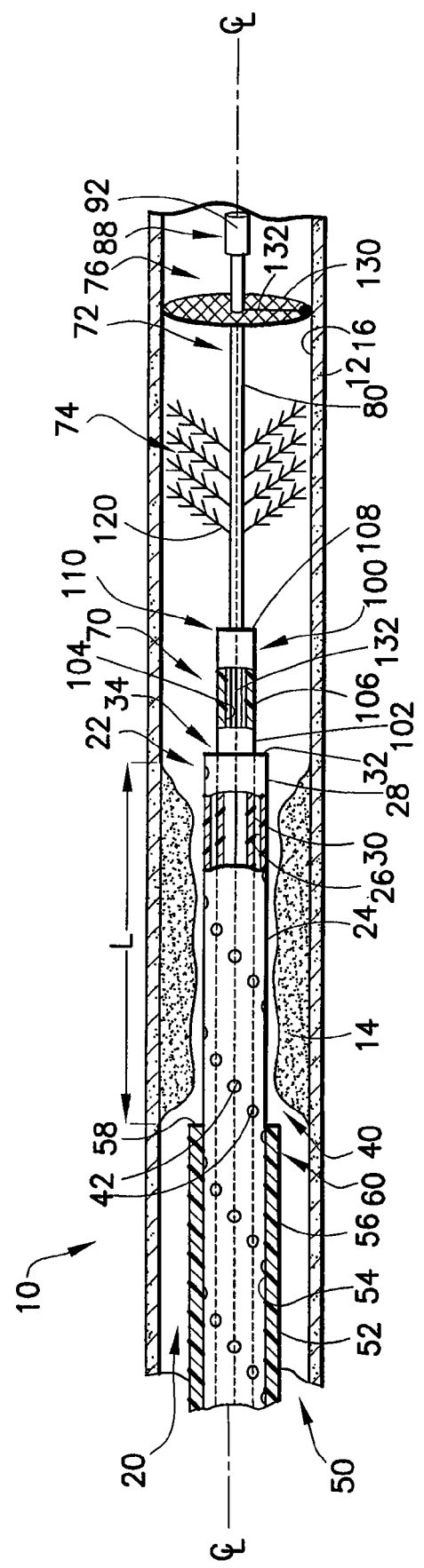
FIG. 4 is a longitudinal cross-sectional view of the of the distal end portion of the catheter of FIG. 2 showing the filtration element and sensing element each in a fully deployed state.

As will be clear from viewing FIGS. 2-4, as filtering and sensing catheter 72 is deployed distally from inner sheath 100 or, alternatively, inner sheath 100 is retracted proximally relative to filtering and sensing catheter 72, filtration element 74 is exposed from or projects outward from distal opening 114 in end wall 108 of lumenal body 102 of inner sheath 100. As filtration element 74 is exposed, filtration structures 120 begin to deploy as shown in FIG. 3. Filtration structures 120 expand radially outward to their memorized shape with stem portions 122 defining an acute angle with central longitudinal axis $C_L$ of catheter 10. However, filtration structures 120 may form any desirable angle with the central longitudinal axis $C_L$ of catheter 10 and are not limited to an acute angle, although this provides for easy expression of filtration element 74 from inner sheath 100 and subsequent ingress into inner sheath 100 to enable easy removal of second catheter 70 and/or catheter 10 from blood vessel 12. Filtration element 74 has a fully expanded condition shown in FIG. 4 in which the filtration structures 120 stretch radially across blood vessel 12 to filter fluid flow 18 in blood vessel 12. In the expanded condition, filtration element 74 has an inlet or upstream side 126 and an outlet or downstream side 128. It will be clear that filtration structures 120 are disposed around the circumference of lumenal body 80 of filtering and sensing catheter 72 and, thus, fully encompass 360° of the cross-sectional area of blood vessel 12 to ensure that there is full coverage for thrombotic material 78 dissolved and dislodged from the inner surface 16 of blood vessel 12.

As described previously, sensing element 76 is disposed distal or downstream of filtration element 74. Accordingly, sensing element 76 is in serial relationship and distal to both infusion ports 42 in infusion section 40 of lumenal body 24 of fluid delivery catheter 22 and filtration element 74. Sensing element 76 in one form, as illustrated, is a fine wire mesh 130 formed into the shape of a circle, oval, or other such shape that, when deployed, is positioned across blood vessel 12 and generally matches the cross-sectional shape of blood vessel 12. Sensing element 76 may likewise be made of a flexible solid elastic or superelastic material or a memory metal material which can be preformed into a memorized shape and subsequently deformed into another shape. As with filtration element 74, the expanded or deployed state of sensing element 76 preferably comprises the memorized shape of the sensing element 76. Sensing element 76 is adapted to react with any injected thrombolytic agent A remaining in the fluid stream as represented by arrow 18 in blood vessel 12 after chemical filtration has occurred in filtration element 74 or any compound "D" derived from the injected thrombolytic agent A that is left in the fluid flow 18 after it has passed filtration element 74. Sensing element 76 is also designed to deliver a response signal indicative of and typically proportional to the amount of injected, active thrombolytic agent A left in the fluid flow 18 after it has passed filtration element 74. Sensing element 76 determines the level of remaining thrombolytic agent A by measuring conductivity changes C in wire mesh 130 caused by the interception of thrombolytic agent A in wire mesh 130. Wire mesh 130 is composed of an electrically conductive material of a given resistance. As described previously, when reacting with filtration element 74, the injected thrombolytic agent A desirably binds to the reaction agent on filtration structures 120 thereby chemically trapping or filtering the thrombolytic agent A in the filtration element 74. Any remaining active thrombolytic agent A (see FIG. 9B) reacts with wire mesh 130 which changes the electrical conductivity of the wire mesh 130. Conductivity changes, as represented by arrows C in FIG. 6, are communicated to a feedback device or component 132, in this case a transmitting wire. Depending on the ratio of the area of wire mesh 130 exhibiting conductivity changes C to the cross section of blood vessel 12, assuming wire mesh 130 extends completely across the cross section of blood vessel 12, the total amount of injected thrombolytic agent A in an active state may be determined.

As an alternative, the filtration structures 120 forming filtration element 74 may comprise a chemical coating forming the reaction agent adapted to neutralize or inhibit the thrombolytic agent A and bind the thrombolytic agent A to filtration structures 120 but which also include another agent such as a "sensing" agent which also combines with the thrombolytic agent A. This results in a combined or derived compound D which may be specifically designed or adapted to change the conductivity C of wire mesh 130 in a specific manner. It will be appreciated that the neutralizing or inhibiting agent itself may comprise the "sensing" agent which is specifically adapted to change the conductivity C of wire mesh 130 in a specific manner. In this alternative sensing arrangement, depending on the ratio of the area of wire mesh 130 exhibiting conductivity changes C due to the derived compound D to the cross section of blood vessel 12, the total amount of injected thrombolytic agent A neutralized may be determined. From the total amount of thrombolytic agent A neutralized, the total remaining amount of injected thrombolytic agent A still in an active state may be determined by mathematical calculation. In the schematic illustration in FIG. 10B, thrombolytic agent A is injected into blood vessel 12 and is neutralized or inhibited by an agent, for example, coated on filtration structures 120. The new or derived compound D formed upon filtration is a combination of thrombolytic agent, a neutralizing/inhibiting agent, and, optionally, a conductivity-changing agent.

When this new "derived" compound, identified D comes into contact with wire mesh 130 forming sensing element 76, the conductivity-changing component or molecules of derived compound D will come into contact with current-conducting wire mesh 130 of sensing element 76 and decrease conductivity C of wire mesh sensing element 76. This process is similar to that as described previously with respect to thrombolytic agent A passing to sensing element 76 (as in FIG. 9B). However, the conductivity-changing component of derived compound D may be adapted to elicit a specific conductivity-changing response in wire mesh 130 from which the amount of thrombolytic agent A remaining in an active state may be determined.

As indicated previously, wire mesh 130 forming sensing element 76 may be sized such that it fills the entirety of the cross section of the blood vessel 12. In this configuration, wire mesh 130 may act as an embolus/thrombus catching device as well to prevent the progression of thrombolytic material 78 to a downstream location in blood vessel 12. While sensing element 76 was described hereinabove as a wire mesh 130 that works on the principle of conductivity changes C to sense the level of active or neutralized thrombolytic agent A in blood vessel 12 downstream of filtration element 74, this specific configuration is not intended to be limiting. Sensing element 76 may operate on a principle of resonant mass detection element (Coriolis flow meter), or on an optical reflectance principle, for example fluoroscopy or spectroscopy, as described herein in connection with FIG. 14. A suitable Coriolis flow meter for use as sensing element 76 and in place of wire mesh 130 is manufactured by Emerson Process Management and sold under the trademark Micro Motion® F-Series Mass Flow and Density Meters. Another suitable mass flow meter for use in place of wire mesh 130 is manufactured by Integrated Sensing Systems, Inc. and sold under the trade name ISSYS micro-density meter. Such mass flow meters are used for chemical and/or biological detection.

Moreover, sensing element 76 may further be adapted to sense the amount of therapeutic agent A via thermal detection principles such as injecting the therapeutic agent A at a temperature higher or lower than human body temperature and measuring thermal changes in the physiological fluid in the body lumen. Ion selective electrodes may also be used as part of sensing element 76 or as sensing element 76 itself, and measure the amount of therapeutic agent A based on ion detection principles.

Feedback component 132 in the illustrated embodiment is a conducting wire which is used as a means to carry/deliver a sensing element signal to the proximal terminus of catheter 10 or some point nearby which is external to a patient's body. This sensing element signal delivered is proportional to the amount of remaining thrombolytic agent A in an active state sensed by sensing element 76 or the amount of neutralized or inhibited thrombolytic agent A and now in the form of derived compound D from which the amount of active thrombolytic agent A remaining may be determined. In the illustrated embodiment, feedback component 132 is a conducting wire that is housed within second lumen 86 defined by lumenal body 80 of filtering and sensing catheter 72 and is desirably not in contact with the lumen body 80, and is otherwise protected/encased from outside conductive influences. Feedback component 132 terminates at the proximal terminus of catheter 10 and is connected to a control device 134 such as a computer and/or a display device 136 or another similar type user interface device. As shown in FIG. 1, control device 134 includes a hand-held control device or controller 138 which may be used to control operation of catheter, for example, to extend and retract inner or second catheter 70 relative to outer or first catheter 20 and vice versa. Additionally, hand-held control device 138 may be used to control the extension and retraction of fluid delivery catheter 22 relative to outer sheath 50 and vice versa, filtering and sensing catheter 72 relative to inner sheath 50 and vice versa and, if desired, inner sheath 100 relative to fluid delivery catheter 22 and vice versa.

Referring, in particular, to FIG. 7, a cross-sectional view of a proximal portion 140 of catheter 10 is shown. This view shows control features for the respective first and second catheter assemblies 20, 70 which allow the axial extension or retraction of second or inner catheter assembly 70 relative to first or outer catheter assembly 20 and vice versa by the operator of catheter 10. As shown in FIG. 7, a first collar 142 is provided at the proximal end 62 of lumenal body 52 of outer sheath 50 for manipulating outer sheath 50 relative to lumenal body 24 of fluid delivery catheter 22. Likewise, a second collar 144 is provided at the proximal end 36 of lumenal body 24 of fluid delivery catheter 22 for manipulating fluid delivery catheter 22 relative to outer sheath 50. Additionally, an infusion lumen or luer 146 is provided in lumenal body 24 of fluid delivery catheter 22 to provide thrombolytic agent A to first lumen 30 defined by lumenal body 24 of fluid delivery catheter 22. Such infusion luer 146 may be connected in an infusion pump (not shown) or other device adapted to supply a continuous flow of thrombolytic agent A on demand to first lumen 30.

As further shown in FIG. 7, inner sheath 100 at its proximal end 112 is joined, for example, adhesively to a tubular body 148 which includes a distal end 150 disposed in second collar 144 associated with fluid delivery catheter 22. The joint connection between inner sheath 100 and tubular body 148 permits inner sheath 100 to be manipulated relative to fluid delivery catheter 22 for extending and retracting inner sheath relative to fluid delivery catheter 22. Moreover, the proximal end 90 of lumenal body 80 of filtering and sensing catheter 72 is attached to a plug member 152 which is movably disposed within a central passage 154 in tubular body 148. Plug member 152 permits the axial movement of filtering and sensing catheter 72 within inner sheath 100. In FIG. 7, it will be appreciated that each of the fluid delivery catheter 22, outer sheath 50, filtering and sensing catheter 72, and inner sheath 100 are extended to their substantially distal-most position resulting generally in the configuration of catheter elements shown in FIG. 4, for example. O-rings, as illustrated, may be provided between the proximal end 62 of lumenal body 52 of outer sheath 50 and lumenal body 24 of fluid delivery catheter 22, and between the proximal end 36 of lumenal body 24 and the lumenal body 102 of inner sheath 100 to prevent thrombolytic agent A from leaking from the proximal portion 140 of catheter 10. Further, FIG. 7 illustrates that lumenal body 80 of filtering and sensing catheter 72 may extend through and outward from plug member 152 and continue to enclose feedback component 132 through to connection to control device 134 and/or display device 136.

Referring additionally to FIGS. 8-11, exemplary use of catheter 10 in performing thrombolysis on thrombus 14 will now be described. Prior to using catheter 10 to perform thrombolysis, a medical practitioner may elect to determine the size of thrombus 14 in blood vessel 12 using known cardio-vascular imaging techniques. This allows for the determination of the axial length L of thrombus 14 and the axial length of infusion section 40 of lumenal body 24 of fluid delivery catheter 22 which will be needed to infuse thrombolytic agent A into the vicinity of thrombus 14. Once the size and location of thrombus 14 is determined, catheter 10 may be deployed into blood vessel 12.

Catheter 10 is inserted into blood vessel 12 in a known manner. According to one exemplary manner, a guide wire (not shown) is advanced into blood vessel 12 to the location of thrombus 14. First catheter 20 is then advanced over the guide wire to a position just proximal to thrombus 14. At this point, lumenal body 24 of filtering and sensing catheter 22 may be moved distally forward so that infusion section 40 is uncovered and placed adjacent thrombus 14 which places infusion ports 42 adjacent the thrombus 14. The guide wire is then removed and second catheter 70 is advanced distally through first catheter 20. Inner sheath 100 of second catheter 70 is extended distally from fluid delivery catheter 22 to an extended position distal of thrombus 14 as illustrated. Thereafter, filtering and sensing catheter 72 may be deployed in the manner described previously. When deployed, filtration element 74 is located distal of infusion section 40 and, when fully expanded radially, extends across blood vessel 12. Likewise, sensing element 76 is located distal of filtration element 74 and, when fully expanded radially, extends across blood vessel 12 for thrombolytic agent sensing and embolism protection purposes.

Figure 8:
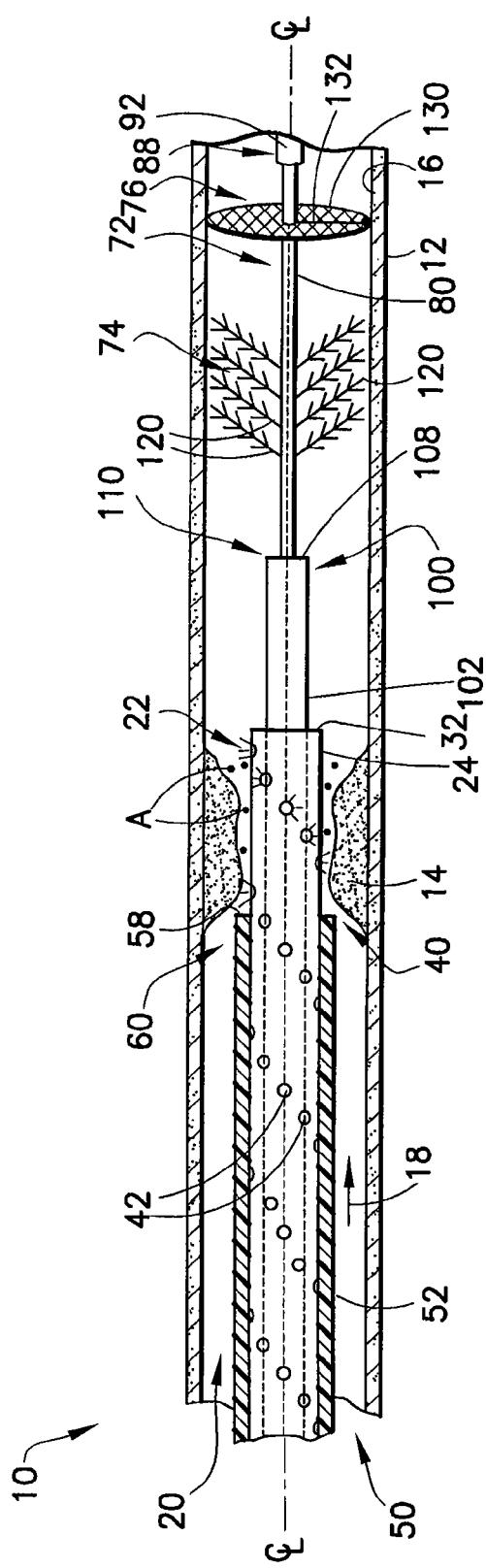
FIG. 8 is a longitudinal cross-sectional view of the distal end portion of the catheter of FIG. 2 showing the delivery of a therapeutic agent within the confines of the blood vessel to treat a thrombus in the blood vessel.

As shown in FIG. 8, thrombolytic agent A is infused through fluid delivery catheter 22 via lumen 30. The thrombolytic agent A passes through lumen 30 in annular space 46 defined between fluid delivery catheter 22 and inner sheath 100. Thrombolytic agent A passes through infusion ports 42 in infusion section 40 of lumen body 24 of fluid delivery catheter 22 and against thrombus 14 in blood vessel 12. Infusion ports 42 may be nozzles to direct the thrombolytic agent A radially outward against the thrombus 14. The force of the flow of thrombolytic agent A in combination with the chemically active ingredients in the thrombolytic agent A causes the thrombus 14 to dissolve and dislodge, typically in pieces or fragments 78, from inner surface 16 of blood vessel 12. Thrombus 14 breaks into fragments of dislodged thrombotic material 78 which travel with natural fluid flow 18 in blood vessel 12 toward filtration element 74. Further, the thrombolytic agent A is formulated to breakdown the thrombotic material 78, causing the thrombotic material 78 to continue to dissolve as it flows with fluid flow 18 distally toward filtration element 74.

Figure 9A:
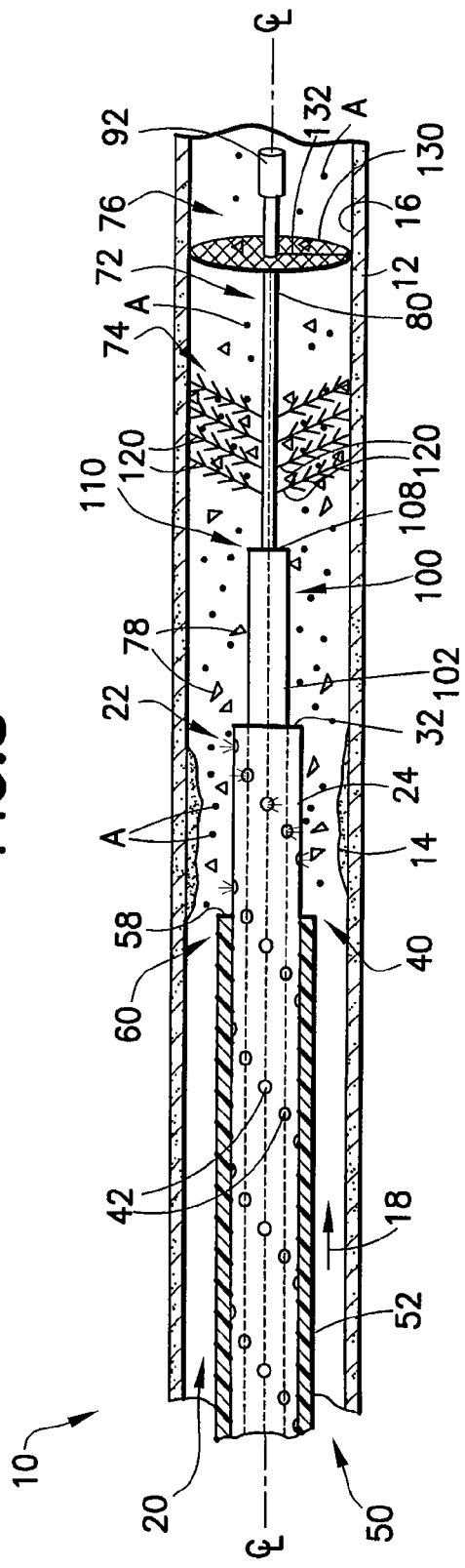
FIG. 9A is a longitudinal cross-sectional view of the distal end portion of the catheter of FIG. 2 showing operation of the catheter in one mode and the results of the delivered therapeutic agent on the thrombus.
Figure 9B:
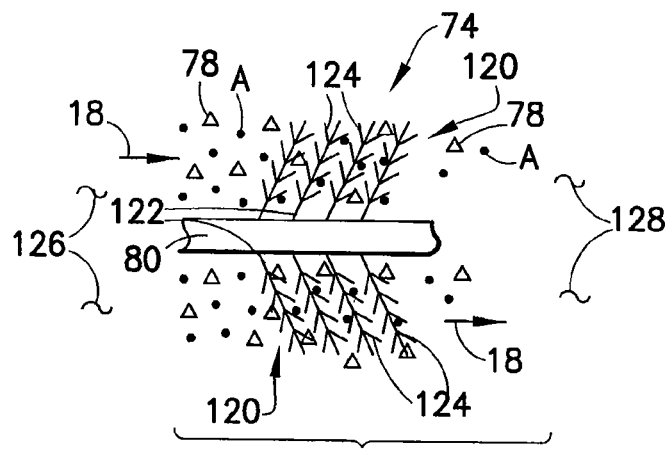
FIG. 9B is schematic view of the operation of the catheter in the mode depicted in FIG. 9A.

Referring to FIGS. 9A-9B, fluid flow 18 carries the fragments of the dislodged thrombotic material 78 toward the inlet side 126 of filtration element 74 and next into filtration structures 120 forming filtration element 74. Likewise, thrombolytic agent A is transported in the same manner towards filtration element 74. As indicated previously, in one embodiment, a chemical coating may be applied to filtration structures 120 which is adapted to neutralize, inhibit, or render harmless or inert the thrombolytic agent A and bind the thrombolytic agent A to filtration structures 120. In the case of tPA as the thrombolytic agent A, the reaction agent used for neutralizing/inhibiting tPA could be: (1) plasminogen activator inhibitor Type 1 (PAI-1), (2) plasminogen activator inhibitor Type 2 (PAI-2), or (3) any other tPA inhibitor. As a result, a majority of the injected active thrombolytic agent A infused through infusion ports 42 in infusion section 40 of lumenal body 24 of fluid delivery catheter 22 is chemically "filtered" or trapped and bound in filtration element 74, as shown schematically in FIGS. 9A-9B. Only a limited amount of active thrombolytic agent A passes filtration element 74 and exits filtration element 74 on its outlet side 128. This limited amount of thrombolytic agent A is carried by the natural fluid flow 18 in blood vessel 12 toward sensing element 76. As will be appreciated from viewing FIGS. 9A-9B, a majority of the dislodged thrombolytic material 78 is trapped by filtration structures 120 of filtration element 74. However, some thrombolytic material 78 may pass filtration element 74 and be carried by natural fluid flow 18 in blood vessel 12 toward sensing element 76 where any remaining thrombolytic material 78 of any consequence is intercepted.

The active thrombolytic agent A that is left in the fluid flow 18 after it has passed filtration element 74 reacts with sensing element 76. As described previously, the level of remaining active thrombolytic agent A downstream of filtration element 74 is determined by measuring the conductivity changes C in wire mesh 130. The conductivity changes C in wire mesh 130 forming sensing element 76 are converted to a sensing element signal that is indicative of and typically proportional to the amount of injected, active thrombolytic agent A left in fluid flow 18 after it has passed filtration element 74. The sensing element signal is carried by feeback component 132 to the proximal end of catheter 10 where control device 134 and, optionally, display device 136 are located in the illustrated embodiment. However, other transmission methods may be used to transmit the sensing element signal to the proximal end of catheter 10 and control device 134 and display device 136 such as wireless transmission between sensing element 76 and control device 134 and/or display device 136 thereby wirelessly coupling sensing element 76 and control device 134 and/or display device 136 together. Control device and/or display device 134, 136 can provide real-time or near real-time quantitative information regarding the amount of thrombolytic agent injected, remaining in the blood vessel 12 downstream of filtration element 74, and/or neutralized based on the sensing element signal. For example, this quantitative information may be communicated to a medical practitioner operating catheter 10 by visual or audible feedback through control device 134 and/or display device 136 In visual form, the information from sensing element signal may be communicated via wires such as by feedback component 132 or wirelessly, as indicated previously, to control device 134 and/or display device 134 which visually displays information regarding the amount of thrombolytic agent A injected, remaining in blood vessel 12 downstream of filtration element 74, and/or neutralized. Control device 134 and/or display device 136 may include a mechanism to audibly convey the information to the operator, such as continuously reciting the amount of active thrombolytic agent A remaining in blood vessel 12, and/or a tactile device, such as hand-held control device 138, to convey the information to the operator tactilely. As shown in FIG. 1, display device 136 may include LED's 156 or a meter 158 which display the information related to the amount of thrombolytic agent A remaining in blood vessel 12 downstream of filtration element 74. It is possible to vary the luminosity of the LED's 156 depending on the amount of thrombolytic agent A present downstream of filtration element 74. If an unsafe amount is detected or determined, the LED's 156 could be made to blink intermittently. Alternative, an audible alarm may be generated by control device 134 and/or display device 136. Moreover, feedback could be generated in hand-held control device 138 if an unsafe level of thrombolytic agent A is detected. For example, the alarm or alert mechanism could be audible with tones of different pitch; a visual alarm could entail the LED's 156 on display device 136 entering an intermittent blinking mode or another visual cue to alert the operator, and such intermittent blinking of data on the display screen of control device 134. Moreover, the alarm or alert could even be tactile, generating a vibrating response in hand-held control device 138 used, for example, to operate catheter 10. Such a tactile response could be through vibration of the hand-held control device 138 and/or increased resistance to movement. It will be appreciated that any combination of visual, audible, and tactile response may be provided based on the sensing element signal. Any unsafe condition determined by control device 134 from the sensing element signal may be used as a basis to change and likely decrease the amount of thrombolytic agent A being delivered and in certain cases could be used as a basis to cease or interrupt delivery of thrombolytic agent A. In such safety conditions, control device 134 may operate automatically to change or cease delivery of thrombolytic agent A.

Figure 10B:
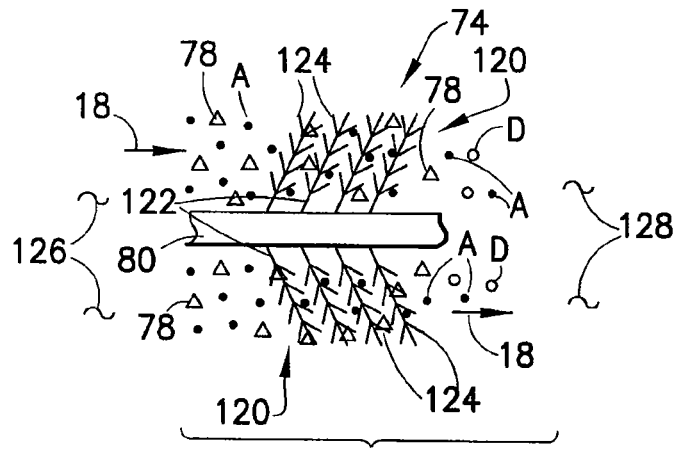
FIG. 10B is schematic view of the operation of the catheter in the mode depicted in FIG. 10A.

Referring to FIGS. 10A-10B, as indicated previously, another possibility is to coat the surfaces of filtration structures 120 forming filtration element 74 with an agent that is a combination of a neutralizing agent and, optionally, a material that facilitates downstream sensing of the "neutralized" thrombolytic agent A by sensing element 76. In this situation, the level of remaining active thrombolytic agent A downstream of filtration element 74 is determined by measuring the conductivity changes C in wire mesh 130 caused by the derived compound D which is combination of thrombolytic agent A, neutralizing or inhibiting agent, and/or an agent adapted to elicit a specific conductivity change C in wire mesh 130. The conductivity changes C in wire mesh 130 forming sensing element 76 are converted in the same manner described previously to a sensing element signal that is now indicative of and typically proportional to the amount of neutralized thrombolytic agent A and now in the form of derived compound D left in fluid flow 18 after it has passed filtration element 74. From the amount of neutralized or inhibited thrombolytic agent A and now in the form of derived compound D detected by sensing element, the amount of active thrombolytic agent A remaining may be determined by mathematical computation. The sensing element signal is now indicative of the amount of derived compound D detected and this is substantially the inverse of the amount of active thrombolytic agent A present downstream of filtration element 74. The sensing element signal is carried by feeback component 132 to the proximal end of catheter 10 where control device 134 and, optionally, display device 136 are located as described previously.

Figure 11B:
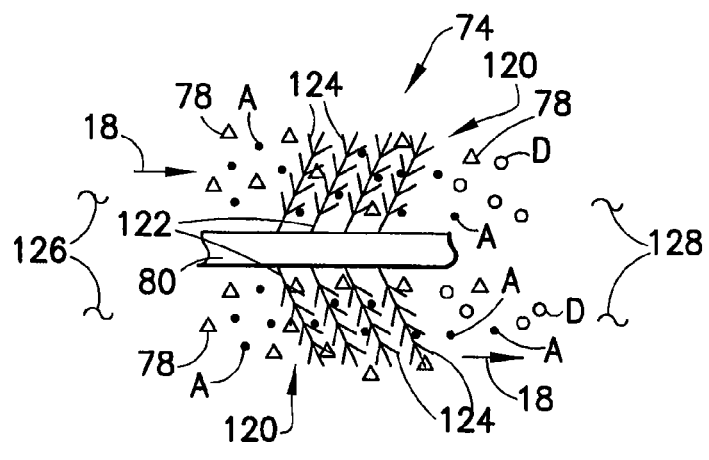
FIG. 11B is schematic view of the operation of the catheter in the mode depicted in FIG. 11A.

Referring to FIGS. 11A-11B, another example is to coat the surfaces of filtration structures 120 forming filtration element 74 with an agent that chemically reacts with the thrombolytic agent A and neutralizes the harmful effect of the thrombolytic agent A and converts the thrombolytic agent A into a non-harmful state that may pass downstream without being chemically trapped or bound in the filtration structures 120. In this situation, the derived compound D is harmless or inert and passes freely through wire mesh 130. However, it will be clear that any thrombotic material 78 which passes through filtration element 74 is still caught or trapped by the filtration structures 120 of filtration element 74. Optionally, the derived compound D may be adapted to elicit minimal or no conductivity change C in wire mesh 130 of sensing element 76. However, active thrombolytic agent A is likely still present and may be sensed in the manner described previously in connection with FIGS. 9A-9B. The sensing element signal is now again indicative of the amount of active thrombolytic agent A remaining and the sensing element signal is carried by feedback component 132 to the proximal end of catheter 10 where control device 134 and, optionally, display device 136 are located as described previously.

After most, if not all, of the thrombus 14 is dislodged from the inner surface 16 of blood vessel 12, the flow of thrombolytic agent A through fluid delivery catheter 22 is terminated. Desirably, the flow of thrombolytic agent A during the infusion process breaks down most, if not all, the fragments of thrombotic material 78 trapped in the filtration elements 120 and only a sparse few elements of thrombotic material 78 are trapped by wire mesh 130 of sensing element 76. Having completed the thrombolysis, catheter 10 is then removed from blood vessel 12 by, for example, reversing the steps used to deploy the catheter 10. In particular, filter and sensing catheter 72 may be moved proximally, causing the filtration structures 120 of filtration element 74 to collapse toward the outer surface 84 of lumenal body 80 and substantially parallel to the central longitudinal axis $C_L$ of catheter 10. Any fragments of thrombotic material 78 caught in filtration elements 120 will remain trapped in the collapsed configuration of filtration element 74. Next, the wire mesh 130 of sensing element 76 is collapsed back toward the outer surface 84 of lumenal body 80 of filtering and sensing catheter 72. Filtering and sensing catheter 72 may then be withdrawn into inner sheath 100 completing the reconstitution of second or inner catheter 70. Second catheter 70 is then retracted through first catheter 20 and removed from blood vessel 12. Fluid delivery catheter 22 may be retracted into outer sheath 50 in an analogous manner as the foregoing to complete reconstitution of first or outer catheter 20 and the first catheter 20 may be removed from blood vessel 12 completing the withdrawal of catheter 10 from blood vessel.

Referring to FIG. 13, another embodiment of catheter 10a is shown. In FIG. 13, filtration element 74 is omitted and, substantially in its place, filtering and sensing catheter 72a comprises a second infusion section 160 which operates substantially as the filtration element in this embodiment. Second infusion section 160 includes a plurality of distal infusion ports 162 for delivering an infusate, such as a known thrombolytic agent inhibitor (a reaction agent) for neutralizing or inhibiting the active thrombolytic agent A introduced via infusion section 40a and infusion ports 42a in lumenal body 24a of fluid delivery catheter 22a. In effect, catheter 10a operates in a manner analogous to catheter 10 discussed in connection with FIGS. 11A-11B, wherein filtration structures 120 in filtration element 74 are coated with a solid or liquid coating adapted to neutralize or inhibit the harmful effects of the injected thrombolytic agent A. In the present embodiment, the neutralizing/inhibiting agent is injected downstream and via lumenal body 80a of filtering and sensing catheter 72a and operates to neutralize or inhibit the thrombolytic agent A at substantially the same location where, previously, filtration element 74 was located. However, it will be clear that, if desired, additional thrombolytic agent A may also be infused into blood vessel 12 via lumenal body 80a through infusion section 160 and distal infusion ports 162 to treat, for example, a secondary thrombus (not shown) located distal from thrombus 14 and proximal of sensing element 76a. Additionally, a different type of therapeutic/thrombolytic agent may be infused through infusion section 160, if desired, to treat another condition or abnormality located downstream or distal of thrombus 14.

As with infusion section 40a, distal infusion ports 162 extend from an inner surface 104a through to the outer surface 106a of lumenal body 80a and are spaced axially apart on the lumenal body 80a of filtering and sensing catheter 72a. In accordance with the illustrated embodiment, distal infusion ports 162 extend along lumenal body 80a of filtering and sensing catheter 72a in a helical pattern, but could alternatively extend in another suitable pattern as detailed previously in connection with "upstream" infusion section 40a. Distal infusion ports 162 may vary in size and increase in diameter toward distal end 88a of lumenal body 80a of filtering and sensing catheter 72a, although it should be understood that the sizes of the infusion ports 162 could be changed to another suitable configuration. Distal infusion ports 162 are able to deliver infusate at a flow rate sufficient to neutralize or inhibit substantially all of the thrombolytic agent A delivered into blood vessel 12a via infusion section 40a on lumenal body 24a of fluid delivery catheter 22a. It will be appreciated that feedback component or element 132a is desirably an insulated wire so that feedback component 132a is shielded from conductivity effects of the neutralizing/inhibiting agent or, alternatively, a wireless connection may be used between sensing element 76a and control device 134 and/or display device 136, each shown in FIG. 1. Neutralizing/inhibiting agent is introduced into second lumen 86a defined by lumenal body 80a of filtering and sensing catheter 72a via a suitable delivery port (not shown) incorporated as part of the proximal end 90a (FIG. 7) of lumenal body 80a.

Thrombolysis is performed with catheter 10a using the same general process as described previously with regard to the catheter 10. Once first and second catheters 20a, 70a are positioned as described previously, thrombolytic agent A is infused through fluid delivery catheter 22a via lumen 30a. The thrombolytic agent A passes through lumen 30a in annular space 46a defined between fluid delivery catheter 22a and inner sheath 100a. Thrombolytic agent A passes through infusion ports 42a in infusion section 40a of lumen body 24a of fluid delivery catheter 22a and against thrombus 14a in blood vessel 12a.

Meanwhile and at about the same time neutralizing/inhibiting agent is directed through distal infusion ports 162 from second infusion section 160 on the lumenal body 80a of filtering and sensing catheter 72a. The infused neutralizing/inhibiting agent counteracts and renders substantially inert the effects of the infused thrombolytic agent A by chemically reacting with the thrombolytic agent A thereby neutralizing the harmful effects of the thrombolytic agent A. As shown in FIG. 13, a combined/derived compound D is formed by the chemical reaction between thrombolytic agent A and neutralizing/inhibiting agent which is carried, harmless, by fluid flow 18a in blood vessel 12 in the direction of sensing element 74a. Neutralizing/inhibiting agent converts the thrombolytic agent A into a non-harmful state "D" that may pass freely through wire mesh 130a of sensing element 76a. However, it will be clear that any released and undissolved thrombotic material 78a remaining in fluid flow 18a is still caught or trapped by the wire mesh 130a of sensing element 76a in the manner described previously. Additionally, to the degree that active thrombolytic agent A is still present downstream of second infusion section 160, this remaining active thrombolytic material may be sensed in the manner described previously in connection with FIGS. 9A-9B.

FIG. 14 illustrates another embodiment of catheter 10b which is substantially similar to catheter 10 discussed in connection with FIGS. 1-6 with certain changes to filtering and sensing catheter 72b to illustrate alternative sensing arrangements for sensing the amount of active thrombolytic agent A in remaining in blood vessel 12b downstream of filtration element 74b. In catheter 10b, sensing element 76b extending from lumenal body 80b of filtering and sensing catheter 72b, which previously in the form of a conductive wire mesh 130, is replaced by a pair of light-sensing fiber optic lines 164, 166. Fiber optic lines 164, 166 are disposed within inner sheath 100 and are deployable relative to inner sheath 100 in generally the same manner as filtering and sensing catheter 72b. In one embodiment, fiber optic lines 164, 166 may be secured in some manner, such as by adhesive, to the outer surface 84b of lumenal body 80b of filtering and sensing catheter 72b such that they are deployed simultaneously with filtering and sensing catheter 72b. In such a deployed state, fiber optic lines 164, 166 are disposed in the vicinity of filtration element 74b and filtration structures 120b in particular to monitor the filtration element 74b and the amount of thrombolytic agent A present downstream or passing filtration structures 120b. As shown in FIG. 14, a distal end of each fiber optic line 164, 166 is orientated and desirably biased in the direction toward filtration structures 120b to monitor the area downstream of filtration structures 120b and the thrombolytic agent A passing filtration element 74b. Accordingly, sensing element 76b, in the present embodiment, is adapted to sense the amount of active thrombolytic agent A present (or neutralized) in blood vessel 12b downstream of filtration element 74b via reflectance principles (i.e., fluoroscopy or spectroscopy). As an example, as chemical filtration occurs in filtration element 74b in the manner described previously, the chemical reaction in which thrombolytic agent A is neutralized or inhibited will provide a definitive change in light reflectance which may be monitored by fiber optic lines 164, 166. From the resulting change in reflectance, the amount of thrombolytic agent A neutralized/inhibited may be determined. From this determination, a mathematical computation provides the amount of active thrombolytic agent A remaining in blood vessel 12b downstream of filtration element 74b.

Additionally, as illustrated a filter basket 168 is provided downstream of filtration element 74b in the general area previously occupied by sensing element 76 discussed previously. Filter basket 168 guards against fragments of thrombotic material 78b traveling unchecked through blood vessel 12b downstream from filtration element 74b. A suitable filter basket for used as filter basked 168 is disclosed in U.S. Pat. No. 6,755,813 to Ouriel et al. which is incorporated by reference herein in its entirety. It is within the scope of this embodiment to include the "sensing" function described previously in connection with sensing element 76 within the wire mesh framework of filter basket 168 or even to dispose sensing element 76 within the body of filter basket 168 as an alternative. Other than the addition of filter basket 168 and the use of fiber optic lines 164, 166 in place of sensing element 76, all other aspects of catheter 10b are consistent with catheter 10 discussed in connection with FIGS. 1-6.

As described previously, catheter 10 and its use are not limited to the delivery of thrombolytic agent A to blood vessel 12 described hereinabove. Catheter 10 may have other applications one example of which is for the delivery of chemotherapeutic agent (doxorubicin) A to the location of malignant cancer tumors in a body lumen, cavity, and the like. Chemotherapy agents A have been used successfully in many cases to treat malignant tumors but current delivery techniques have several limitations. Additionally, these agents themselves do not affect tumor cell growth selectively, leading to high toxicity and undesirable side effects. For examples, doxorubicin is a widely used anti-cancer agent. Doxorubicin is used to treat breast cancer ovarian cancer, transitional cell bladder cancer, bronchogenic lung cancer, thyroid cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma related to acquired immunodeficiency syndrome (AIDS), among others. Some common commercial names for doxorubicin are Doxil, Rubex, and Adriamycin. Doxil is doxorubicin HCL encapsulated in long-circulating (stealth) liposomes. These liposomes are formulated with surface-bound methoxypolyethylene glycol (MPEG), a process referred to as PEGylation.

Doxorubicin has a strong anit-proliferative effect over a large panel of solid tumors. Doxorubicin intercalates into DNA and breaks the strands of double helix by inhibiting topoisomerase II. Despite its clinical efficacy, Doxorubicin is not tumor selective and therefore affects healthy tissue. In so doing, doxorubicin causes severe side effects. Currently, Doxorubicin is administered intravenously as an infusion over some period of time (dependent upon concentration and other factors). As such, there is a systemic application of the drug and high cellular collateral damage. Toxic side effects of systemically delivered doxorubicin include nausea and vomiting which may last up to 24-48 hours after treatment, loss of appetite, diarrhea, difficulty swallowing, thinned or brittle hair, skin irritation (sunburn-like) or rash on areas previously exposed to radiation treatments, darkening of fingernails or toenails, swelling, pain, redness, or peeling of skin on the palms and soles of the feet.

Referring to FIGS. 1-6 again, catheter 10 would operate in much the same manner with doxorubicin as the chemotherapy agent A as described previously with the administered therapeutic agent being thrombolytic agent A such as tPA. In this specific use case, catheter 10 is inserted into a patient's vascular system, generally through the femoral artery. Catheter 10 is maneuvered through the vascular system until it is positioned in proximity to the tumor or cancerous tissue. Chemotherapy agent A is infused through fluid delivery catheter 22 via lumen 30. The chemotherapy agent A passes through lumen 30 in annular space 46 defined between fluid delivery catheter 22 and inner sheath 100. Chemotherapy agent A passes through infusion ports 42 in infusion section 40 of lumen body 24 of fluid delivery catheter 22 and against the tumor (not shown) which will be located in the location of thrombus 14 in FIGS. 2-4. Infusion ports 42 may be nozzles to direct the chemotherapy agent A radially outward against the tumor. The chemotherapy agent A then travels in fluid flow 18 past the target area of cancerous tissue to some point distal, to filtration element 74.

Figure 12:
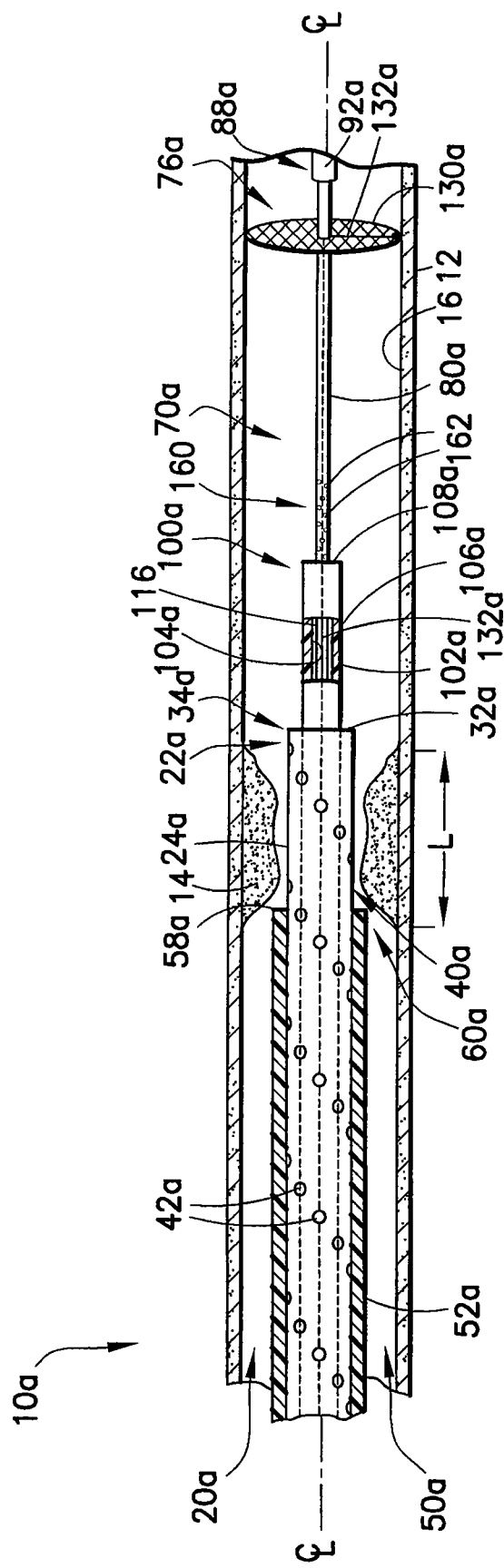
FIG. 12 is a longitudinal cross-sectional view of the catheter of FIG. 1 according to another embodiment.

In contrast to the previous example associated with FIGS. 2-4 wherein thrombolytic agent A comprises the therapeutic agent, chemotherapy agent A may or may not release fragments of tumor into fluid flow 18. However, any such releases or fragments of dislodged tumor material are intercepted by filtration structures 120 forming filtration element 74. The chemotherapy agent A is transported in the same manner as described previously as thrombolytic agent A, by fluid flow 18, towards filtration element 74. In the present embodiment, a chemical coating is also applied to filtration structures 120 which is adapted to neutralize, inhibit, or render harmless or inert the chemotherapy agent A and bind the chemotherapy agent A to filtration structures 120. In the case of doxorubicin as the chemotherapy agent A, the neutralizing/inhibiting (i.e., reaction) agent includes mononuclear phagocytes. As a result, a majority of the injected chemotherapy agent A infused through infusion ports 42 in infusion section 40 of lumenal body 24 of fluid delivery catheter 22 is chemically "filtered" or trapped/bound in filtration element 74. Only a limited amount of active chemotherapy agent A passes filtration element 74 and exits filtration element 74 on its outlet side 128. This limited amount of chemotherapy agent A is carried by the natural fluid flow 18 in blood vessel 12 toward sensing element 76. The active chemotherapy agent A that is left in the fluid flow 18 after it has passed filtration element 74 reacts with sensing element 76 in the manner described previously in connection with thrombolytic agent A, (See FIGS. 9A-9B). Briefly, as described previously, the level of remaining active chemotherapy agent A downstream of filtration element 74 is determined by measuring the conductivity changes C in wire mesh 130. The conductivity changes C in wire mesh 130 forming sensing element 76 are converted to a sensing element signal that is indicative of (i.e., proportional to) the amount of injected, active chemotherapy agent A left in fluid flow 18 after it has passed filtration element 74. The sensing element signal is carried by feedback component 132 to the proximal end of catheter 10 where control device 134 and, optionally, a display device 136 are located in the illustrated embodiment. Chemotherapy agent A may also be treated in the manner described previously in connection with FIGS. 10A-10B and 11A-11B described previously. Additionally, the embodiments of catheter 10a, 10b shown in FIGS. 12-13 and 14 respectively may be used to treat and neutralize chemotherapy agent A in the manner described previously in this disclosure.

Due to the ability to neutralize doxorubicin, more concentrated doxorubicin can be released without fear of causing systemic toxic reactions. Toxic reactions will be limited to that area between infusion section 40 of lumenal body 24 of fluid delivery catheter 22 and filtration element 74. This has the potential of decreasing the number of chemotherapy sessions that a patient must endure.

While several embodiments of a therapeutic agent delivery apparatus and methods associated therewith were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

The invention claimed is:

1. An apparatus for infusing a therapeutic agent into a body lumen, the apparatus comprising:
   a multiple coaxial catheter assembly comprising a first lumenal body;
   a second lumenal body extending beyond the first lumenal body, said second lumenal body having at least one infusion port for infusing the therapeutic agent into the body lumen;
   a third lumenal body extending beyond the second lumenal body;
   a sensing element attached to the third lumenal body distal of the at least one infusion port and adapted to sense an amount of infused therapeutic agent or any compound derived from the therapeutic agent in the body lumen;
   a sensing element signal produced by the sensing element; and
   a feedback component associated with the sensing element and adapted to provide the sensing element signal to a location outside of the body lumen.

2. The apparatus of claim 1, wherein the feedback component provides the sensing element signal to a user interface.

3. The apparatus of claim 1, wherein the sensing element signal is represented to a user as an audible, visual, or tactile stimulus or a combination stimulus comprising one or more of the audible, visual, and tactile stimuli.

4. The apparatus of claim 1, wherein the sensing element signal is proportional to the amount of infused therapeutic agent or derivative thereof detected by the sensing element.

5. The apparatus of claim 1, wherein the sensing element is adapted to sense the amount of therapeutic agent or derivative thereof by one or more of resonant mass detection, light reflectance, and electrical conductivity changes.

6. The apparatus of claim 1, wherein the sensing element is shaped to correspond to the cross-sectional shape of the body lumen.

7. The apparatus of claim 1, wherein the sensing element is formed as a fine wire mesh.

8. The apparatus of claim 1, wherein the sensing element is formed of electrically conductive material.

9. The apparatus of claim 8, wherein the electrically conductive material is formed as a fine wire mesh adapted to intercept at least some of the therapeutic agent or derivative thereof in the body lumen.

10. The apparatus of claim 8, wherein the electrically conductive material changes conductivity when exposed to the therapeutic agent or derivative thereof.

11. An apparatus for infusing a therapeutic agent into a body lumen, the apparatus comprising:
a multiple coaxial catheter assembly comprising a first lumenal body;
a second lumenal body extending beyond the first lumenal body, the second lumenal body having at least one infusion port for infusing the therapeutic agent into the body lumen;
a third lumenal body extending beyond the second lumenal body;
a sensing element attached to the third lumenal body;
a filtration element distal of the at least one infusion port and adapted to deliver a reaction agent which is adapted to react with the therapeutic agent in the body lumen;
a chemical coating on the filtration element; and
a sensing element signal produced by the sensing element, wherein the sensing element is adapted to sense an amount of infused therapeutic agent or any compound derived from the therapeutic agent in response to the reaction agent in the body lumen.

12. The apparatus of claim 11, wherein the filtration element comprises a plurality of radially expandable structures secured to the third lumenal body.

13. The apparatus of claim 11, wherein the filtration element is in the form of at least one distal infusion port disposed on the third lumenal body.

14. The apparatus of claim 13, wherein the sensing element is distal of the at least one distal infusion port.

15. The apparatus of claim 11, further comprising a feedback component associated with the sensing element and adapted to provide the sensing element signal to a location outside of the body lumen.

16. The apparatus of claim 15, wherein the feedback component is adapted to communicate wirelessly with a user interface located outside of the body lumen.

17. The apparatus of claim 15, wherein the feedback component provides the sensing element signal to a user interface.

18. The apparatus of claim 15, wherein the sensing element signal is represented to a user as an audible, visual, or tactile stimulus or a combination stimulus comprising one or more of an audible, visual, and tactile stimuli.

19. The apparatus of claim 15, wherein the sensing element signal is proportional to the amount of infused therapeutic agent or derivative thereof sensed by the sensing element.

20. The apparatus of claim 11, wherein the sensing element is adapted to sense the amount of infused therapeutic agent or derivative thereof by one or more of resonant mass detection, light reflectance, and electrical conductivity changes.

21. The apparatus of claim 11, wherein the sensing element is formed as a fine wire mesh.

22. The apparatus of claim 11, wherein the sensing element is formed of electrically conductive material.

23. The apparatus of claim 22, wherein the electrically conductive material is formed as a fine wire mesh adapted to intercept at least some of the infused therapeutic agent or derivative thereof in the body lumen.

24. The apparatus of claim 22, wherein the electrically conductive material changes conductivity when exposed to the infused therapeutic agent or derivative thereof.

25. A multiple coaxial catheter assembly comprising:
a first lumenal body;
a second lumenal body extending beyond the first lumenal body, the second lumenal body having at least one infusion port for infusing a therapeutic agent into a body lumen;
a third lumenal body extending beyond the second lumenal body; and
a sensing element attached to the third lumenal body used to deliver the therapeutic agent to the body lumen, the sensing element comprising an electrically conductive body adapted to change conductivity when exposed to the therapeutic agent or any compound derived from the therapeutic agent.

26. The catheter assembly of claim 25, wherein the electrically conductive body is in the form of an electrically conductive fine wire mesh.

27. The catheter assembly of claim 25, wherein the electrically conductive body is shaped to correspond to a cross-sectional shape of the body lumen.

28. The catheter assembly of claim 25, wherein the sensing element further comprises a feedback component adapted to provide a sensing element signal to a location outside of the body lumen.

29. The catheter assembly of claim 28, wherein the sensing element further comprises a user interface coupled to the feedback component for receiving the sensing element signal.

30. The catheter assembly of claim 29, wherein the user interface is adapted to represent the sensing element signal to a user as an audible, visual, or tactile stimulus or a combination stimulus comprising one or more of the audible, visual, and tactile stimuli.

31. The catheter assembly of claim 28, wherein the sensing element signal is proportional to an amount of therapeutic agent or derivative thereof sensed by the sensing element.

32. The catheter assembly of claim 25, wherein the sensing element is adapted to sense a combination of the therapeutic agent and a reaction agent adapted to react with the therapeutic agent.

33. A multiple coaxial catheter assembly comprising:
a first lumenal body;
a second lumenal body extending beyond the first lumenal body, the second lumenal body having at least one infusion port for infusing a therapeutic agent into a body lumen;
a third lumenal body extending beyond the second lumenal body; and
a filtration element attached to the third lumenal body used to deliver the therapeutic agent to the body lumen, the filtration element comprising a plurality of structures coated with a reaction agent adapted to react with the therapeutic agent.

34. The catheter assembly of claim 33, wherein the plurality of coated structures are radially expandable structures secured to the third lumenal body.

* * * * *

UNITED STATES PATENT AND TRADEMARK OFFICE
CERTIFICATE OF CORRECTION

PATENT NO. : 8,876,754 B2  Page 1 of 1
APPLICATION NO. : 11/469054
DATED : November 4, 2014
INVENTOR(S) : Ranchod et al.

It is certified that error appears in the above-identified patent and that said Letters Patent is hereby corrected as shown below:

ON THE TITLE PAGE:
On Page 3, Item (56), under "OTHER PUBLICATIONS", in Column 1, Line 2, delete "Minature" and insert -- Miniature --, therefor.

IN THE SPECIFICATION:
In Column 1, Line 8, delete "filed" and insert -- field --, therefor.
In Column 1, Line 50, delete "revasculaturization," and insert -- revascularization, --, therefor.
In Column 5, Line 63, delete "agent" and insert -- agent. --, therefor.
In Column 6, Line 4, delete "an" and insert -- a --, therefor.
In Column 7, Line 23, delete "intralumenal" and insert -- intraluminal --, therefor.
In Column 7, Line 52, delete "is schematic" and insert -- is a schematic --, therefor.
In Column 7, Line 58, delete "is schematic" and insert -- is a schematic --, therefor.
In Column 7, Line 64, delete "is schematic" and insert -- is a schematic --, therefor.
In Column 12, Line 21, delete "infuisate," and insert -- infusate, --, therefor.
In Column 20, Line 15, delete "feeback" and insert -- feedback --, therefor.
In Column 20, Line 36, delete "display device 134" and insert -- display device 136 --, therefor.
In Column 21, Line 36, delete "feeback" and insert -- feedback --, therefor.
In Column 24, Line 65, delete "anit-proliferative" and insert -- anti-proliferative --, therefor.

IN THE CLAIMS:
In Column 26, Line 38, in Claim 1, delete "body, said" and insert -- body, the --, therefor.
In Column 27, Line 7, in Claim 9, delete "the therapeutic" and insert -- the infused therapeutic --, therefor.
In Column 27, Line 11, in Claim 10, delete "therapeutic" and insert -- infused therapeutic --, therefor.

Signed and Sealed this
Twenty-fourth Day of March, 2015

Michelle K. Lee
*Director of the United States Patent and Trademark Office*